(12) United States Patent
Suzuki

(10) Patent No.: US 10,695,531 B2
(45) Date of Patent: Jun. 30, 2020

(54) BALLOON CATHETER AND MEDICAL ELONGATED BODY

(71) Applicant: TERUMO KABUSHIKI KAISHA, Shibuya-ku, Tokyo (JP)

(72) Inventor: Kenta Suzuki, Shizuoka (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 177 days.

(21) Appl. No.: 16/013,220

(22) Filed: Jun. 20, 2018

(65) Prior Publication Data

US 2018/0296795 A1  Oct. 18, 2018

Related U.S. Application Data

(63) Continuation of application No. PCT/JP2016/087837, filed on Dec. 19, 2016.

(30) Foreign Application Priority Data

Dec. 21, 2015 (JP) .................. 2015-249048
Dec. 21, 2015 (JP) .................. 2015-249050

(51) Int. Cl.
*A61M 25/00* (2006.01)
*B29C 48/153* (2019.01)
(Continued)

(52) U.S. Cl.
CPC ........ *A61M 25/0021* (2013.01); *A61M 25/00* (2013.01); *A61M 25/005* (2013.01);
(Continued)

(58) Field of Classification Search
CPC ............ A61M 2025/006; A61M 25/00; A61M 25/0012; A61M 25/0021; A61M 25/005;
(Continued)

(56) References Cited

U.S. PATENT DOCUMENTS 5,244,619 A    9/1993  Burnham
5,879,342 A *  3/1999  Kelley ................ A61M 25/005
                                                    600/524

(Continued)

FOREIGN PATENT DOCUMENTS

JP        6-7450 A     1/1994
JP     6-511162 A    12/1994
(Continued)

OTHER PUBLICATIONS

English translation of Written Opinion of the International Searching Authority dated Apr. 11, 2017, in corresponding International Application No. PCT/JP2016/087837 (11 pages).

(Continued)

*Primary Examiner* — Rebecca E Eisenberg
(74) *Attorney, Agent, or Firm* — Buchanan Ingersoll & Rooney PC

(57) ABSTRACT

An inner tube includes a tubular body made of a first resin and a reinforcing member disposed on an inner side of the tubular body. The reinforcing member is configured of a linear body including a second resin. The inner tube has a first region including a distal portion provided with a distal opening portion and a second region that is disposed to be closer to a proximal side than the first region. The linear body projects inwardly from the inner surface of the tubular body in the first and second regions, and inwardly projects less in the first region than in the second region. In a balloon catheter, guide wire operability is improved and problems which can arise when using a metal reinforcing member are avoided. In a medical elongated body, sliding resistance of a medical device inserted in a lumen can be reduced.

20 Claims, 13 Drawing Sheets

(51) Int. Cl.
  *A61M 25/10* (2013.01)
  *A61M 25/01* (2006.01)
  *B29C 37/00* (2006.01)
  *B29C 48/09* (2019.01)
  *B29C 48/21* (2019.01)
  *B29L 31/00* (2006.01)

(52) U.S. Cl.
  CPC ........ *A61M 25/0012* (2013.01); *A61M 25/01* (2013.01); *A61M 25/10* (2013.01); *B29C 37/0053* (2013.01); *B29C 48/153* (2019.02); *A61M 2025/006* (2013.01); *B29C 48/09* (2019.02); *B29C 48/21* (2019.02); *B29L 2031/7543* (2013.01)

(58) Field of Classification Search
  CPC .... A61M 25/01; A61M 25/10; A61M 25/104; A61M 25/1006; A61M 25/0054; A61M 25/0043; A61M 25/0053
  See application file for complete search history.

(56) References Cited

U.S. PATENT DOCUMENTS

| | | | |
|---|---|---|---|
| 6,511,462 B1 | 1/2003 | Itou et al. | |
| 2001/0027310 A1* | 10/2001 | Parisi | A61L 29/085 604/524 |
| 2005/0010169 A1* | 1/2005 | Kuhlein | A61M 25/0023 604/93.01 |
| 2006/0030835 A1 | 2/2006 | Sherman et al. | |
| 2006/0178653 A1* | 8/2006 | Shimogami | A61M 25/0012 604/526 |
| 2012/0253447 A1* | 10/2012 | Hayasaka | A61F 2/958 623/1.11 |
| 2016/0279385 A1* | 9/2016 | Katsurada | A61M 25/0108 |

FOREIGN PATENT DOCUMENTS

| | | |
|---|---|---|
| JP | 2001-87389 A | 4/2001 |
| JP | 2006-158788 A | 6/2006 |
| JP | 2007-29736 A | 2/2007 |
| JP | 2007-229452 A | 9/2007 |
| JP | 2010-115375 A | 5/2010 |
| JP | 2013-52003 A | 3/2013 |
| JP | 2014-57793 A | 4/2014 |

OTHER PUBLICATIONS

International Search Report (PCT/ISA/210) issued on Japanese, by the "ISA Country " Patent Office as the International Searching Authority for International Application No. PCT/JP2016/087837.

* cited by examiner

BALLOON CATHETER AND MEDICAL ELONGATED BODY

CROSS-REFERENCES TO RELATED APPLICATIONS

This application is a continuation of International Application No. PCT/JP2016/087837 filed on Dec. 19, 2016, and claims priority to Japanese Application No. 2015-249048 filed on Dec. 21, 2015 and Japanese Application No. 2015-249050 filed on Dec. 21, 2015, the entire content of all three of which is incorporated herein by reference.

TECHNICAL FIELD

The present invention generally relates to a balloon catheter and a medical elongated body.

BACKGROUND DISCUSSION

Japanese Patent Application Publication No. 2014-57793 discloses a balloon catheter as a medical device that widens a stenosed site formed in a living body.

It is desirable that a medical instrument having a relatively elongated shape like a balloon catheter has a desired physical property such that a kink, breaking, or the like does not occur when the device is used in a living body. For example, with a guiding catheter, a microcatheter, or the like, an attempt to improve kink resistance (prevention of occurrence of folding during bending) or a tensile strength by embedding a metal reinforcing member such as a coil in a resin tube has been made. Similarly, with the balloon catheter, it is considered that it is possible to improve the kink resistance or the tensile strength by adding a metal reinforcing member to a shaft.

SUMMARY

However, in a case of using a metal reinforcing member, compatibility between the reinforcing member and the shaft of the balloon catheter configured of a resin material is low, and thus it is difficult to achieve a sufficient bonding force therebetween. In addition, when a distal tip is attached to impart flexibility to a distal portion of the shaft, it is necessary to perform an end-portion treatment such that the metal reinforcing member is not dispersed on an end portion of the shaft.

On the other hand, regarding the shaft of the balloon catheter, there is a problem in terms of operability of a guide wire such as a decrease in sliding resistance of the guide wire inserted into a guide wire lumen or the improvement in insertability of the guide wire through the guide wire lumen.

The balloon catheter disclosed here makes it possible to improve operability of a guide wire and to prevent various problems which can arise in a case of using a metal reinforcing member from arising.

Also disclosed here is a medical elongated body by which it is possible to decrease sliding resistance of a medical device that is inserted through a lumen and it is possible to prevent various problems which can arise in a case of using a metal reinforcing member from arising.

According to one aspect, a balloon catheter comprises: an outer tube that includes a lumen; an inner tube disposed in the lumen of the outer tube, with the inner tube comprising a tubular body possessing an open proximal end and an open distal end, and the tubular body including a guide wire lumen that communicates with both the open proximal end and the open distal end and through which a guide wire is insertable; and an outwardly expandable balloon fixed to a distal portion of the inner tube and a distal portion of the outer tube. The tubular body is comprised of a first resin and a reinforcing member disposed on an inwardly facing surface of the tubular body that faces toward the guide wire lumen. The reinforcing member includes a linear body comprised of a second resin that is different form the first resin, wherein the linear body projects inwardly from the inwardly facing surface of the tubular body. The inner tube including a first region at a distal portion of the inner tube, with a part of the distal portion of the inner tube including the open distal end. The inner tube also comprises a second region positioned proximal of the first region. The reinforcing member is located in the first region of the inner tube and in the second region of the inner tube, and the linear body projects inwardly from the inwardly facing surface of the tubular body less in the first region of the inner tube than in the second region.

According to another aspect, a balloon catheter comprises: an outer tube that includes a lumen; an inner tube disposed in the lumen of the outer tube, with the inner tube comprising a tubular body possessing an open proximal end and an open distal end, and the tubular body including a guide wire lumen that communicates with both the open proximal end and the open distal end and through which a guide wire is insertable; and an outwardly expandable balloon fixed to a distal portion of the inner tube and a distal portion of the outer tube. The tubular body is comprised of a first resin and a reinforcing member disposed on an inwardly facing surface of the tubular body that faces toward the guide wire lumen. The reinforcing member includes a linear body comprised of a second resin that is different form the first resin, with the linear body projecting inwardly from the inwardly facing surface of the tubular body. The inner tube includes a first region at a distal portion of the inner tube, with a part of the distal portion of the inner tube including the open distal end. The inner tube also comprises a second region positioned proximal of the first region. The reinforcing member is located in the first region of the inner tube and in the second region of the inner tube, and the first and second resins of the tubular body in the first region are melt-solidified, and the first and second resins of the tubular body in the second region are melt-solidified. The first and second resins of the tubular body in the first region being more melt-solidified than the first and second resins of the tubular body in the second region.

In addition, according to another aspect, there is provided a medical elongated body including: an elongated catheter main body that includes a lumen, wherein the catheter main body comprises a tubular body made of a first resin and a reinforcing member disposed on an inwardly facing surface of the tubular body that faces toward the lumen of the catheter main body. The reinforcing member is made of a second resin different from the first resin, and the reinforcing member is comprised of a plurality of linear bodies which are braided so that gaps exist between adjacent linear bodies which are braided. The linear bodies each possess an outer circumferential surface. The tubular body includes convex portions that each project inwardly from the tubular body and penetrate a respective one of the gap portions. At least an outer circumferential surface of the linear body is comprised of the second resin, and the first resin is fused with the second resin at locations in which the convex portions penetrate the gap portions. The melting point of the first resin is lower than the melting point of the second resin.

The balloon catheter configured as described above has the kink resistance or tensile strength improved by the reinforcing member provided on the inner side of the tubular body provided in the inner tube. In addition, in the inner tube of the balloon catheter, the first resin and the second resin are melt-solidified in the first region in vicinity of the distal opening portion. Therefore, the inner circumferential surface of the inner tube has relatively small unevenness by the reinforcing member, and thus it is possible to prevent the guide wire from being caught on the reinforcing member in the vicinity of the distal opening portion. On the other hand, the sliding resistance of the guide wire due to the unevenness by the reinforcing member is decreased in the second region on the proximal side more than in the vicinity of the distal opening portion.

Since the tubular body and the reinforcing member of the balloon catheter both include the resin, the tubular body and the reinforcing member are easily fused together, compared to a case where the reinforcing member is formed of metal. Therefore, when an end portion of the inner tube is cut and the distal tip is attached, there is no need to perform an end-portion treatment for preventing dispersion of an end portion of the reinforcing member, and thus it is easy to perform a manufacturing operation.

In addition, the medical elongated body configured as described above has the kink resistance or tensile strength improved by the reinforcing member provided on the inner surface of the tubular body. In addition, when the medical device is inserted into the lumen of the catheter main body, a contact area between the inner surface of the tubular body and the medical device is decreased owing to the reinforcing member (braided linear bodies) disposed on the inner surface of the tubular body. Therefore, the medical device that is inserted into the lumen of the catheter main body has a low sliding resistance against the inner surface of the tubular body.

In addition, since the tubular body and the reinforcing member of the medical elongated body both include the resin, the tubular body and the reinforcing member are easily fused together, compared to a case where the reinforcing member is formed of metal. Further, since the convex portions made of the first resin penetrates the gap portions made of the second resin of which the reinforcing member is configured, and the convex portions are fused, a contact area between the first resin and the second resin increases, and thus it is possible to achieve relatively strong fusion between the tubular body and the reinforcing member.

In addition, the melting point of the first resin, of which the tubular body of the medical elongated body is configured, is lower than the melting point of the second resin included in the reinforcing member. Therefore, when the reinforcing member is disposed in the tubular body, melting of the reinforcing member due to heat of fusion of the first resin and the second resin is suppressed, and thus it is possible to maintain a shape of the reinforcing member. In this manner, it is possible to more suitably exhibit a function of decreasing the sliding resistance of the medical device.

In addition, the reinforcing member of the medical elongated body includes the second resin, and thus the reinforcing member and the tubular body are satisfactorily fused together. In this manner, when an end portion of the catheter main body is cut and the distal tip or the hub is attached, there is no need to perform an end-portion treatment for preventing dispersion of an end portion of the reinforcing member, and thus it is easy to perform a manufacturing operation.

DETAILED DESCRIPTION

Figure 1:
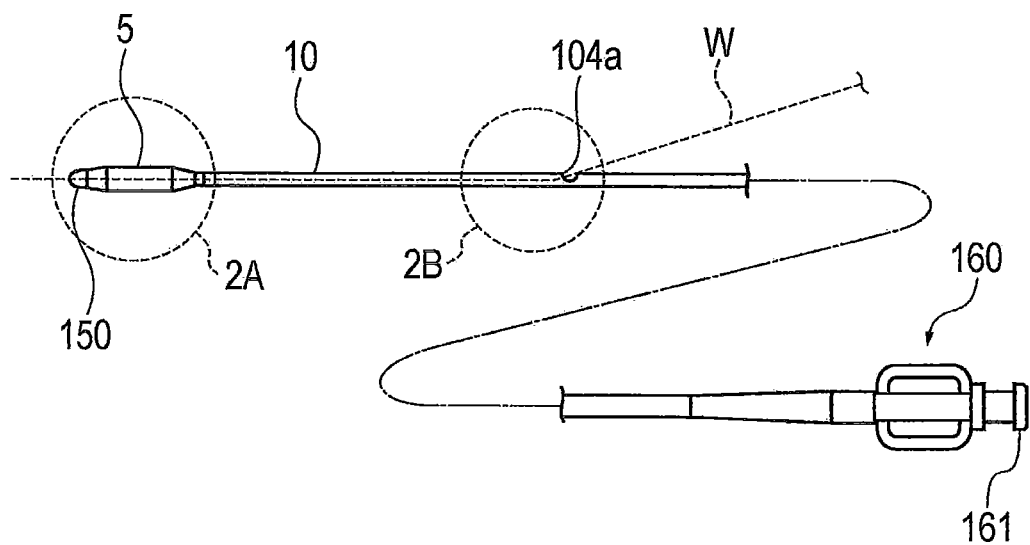
FIG. 1 is a view showing a balloon catheter according to a first embodiment.

Set forth below with reference to the accompanying drawings is a detailed description of embodiments of a balloon catheter and a medical elongated body representing examples of the inventive balloon catheter and medical elongated body disclosed here. The dimensional ratios in the drawing figures is enlarged depending on the description and the ratio may be different from an actual ratio in some cases.

First Embodiment

With reference to FIG. 1, a balloon catheter 1 according to one disclosed embodiment is a medical device that performs a medical treatment by inserting an elongated shaft 10 through a biological organ and dilating a balloon 5 disposed on a distal side or distal end of the shaft 10 in a stenosed site (lesion area) to widen the stenosed site.

In this embodiment disclosed by way of example, the balloon catheter 1 is configured as a PTCA widening balloon catheter that is used to widen a stenosed site of a coronary artery; however, the balloon catheter 1 can be configured to be used for a purpose of performing a medical treatment and a remedy for a biological organ such as a stenosed site formed in another blood vessel, a bile duct, a trachea, an esophagus, another gastrointestinal tract, a urethra, an aurinasal lumen, or another internal organ, or the balloon catheter 1 can be configured as a balloon catheter for delivery which is used for a purpose of conveying a medical instrument such as a stent into a living body.

As shown in FIG. 1, the balloon catheter 1 includes a shaft 10, a balloon 5 that is disposed on a distal end portion of the shaft 10 and is capable of undergoing dilation deformation and deflation deformation depending on inflow and discharge of a pressurizing medium, and a hub 160 disposed on a proximal side or proximal end portion side of the shaft 10.

In the present specification, a side on which a distal tip 150 is disposed in the balloon catheter 1 is referred to as a distal side or distal end, a side on which the hub 160 is disposed in the balloon catheter 1 is referred to as a proximal side ore proximal end, and a direction in which the shaft 10 extends is referred to as an axial direction.

Figure 2A:
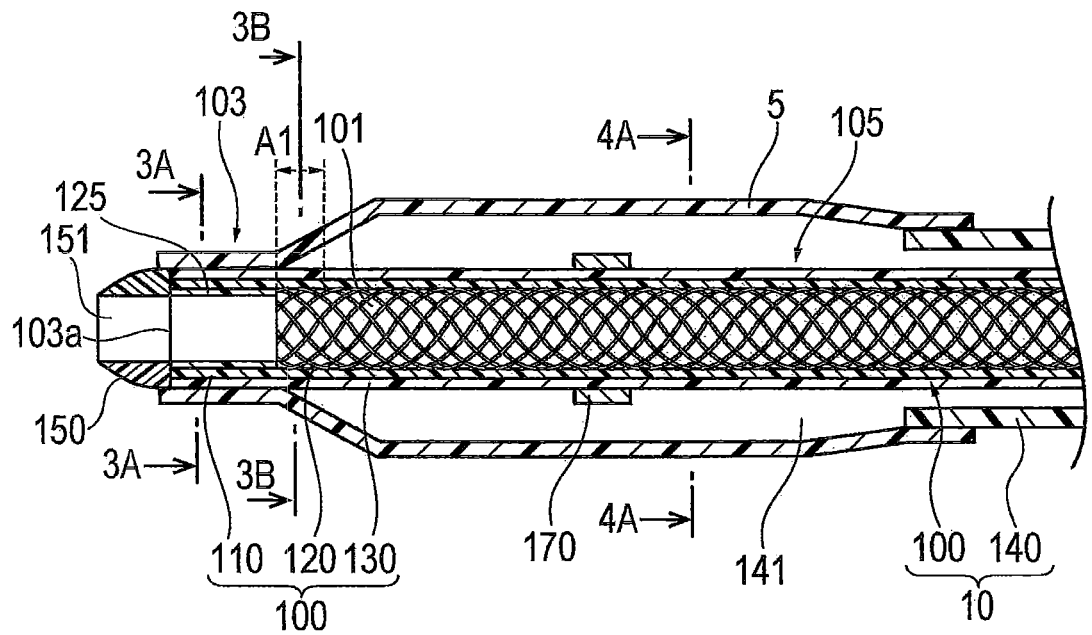
FIG. 2(A) is a view showing a longitudinal cross-section in an axial direction of a part of a dashed line portion 2A shown in FIG. 1.
Figure 2B:
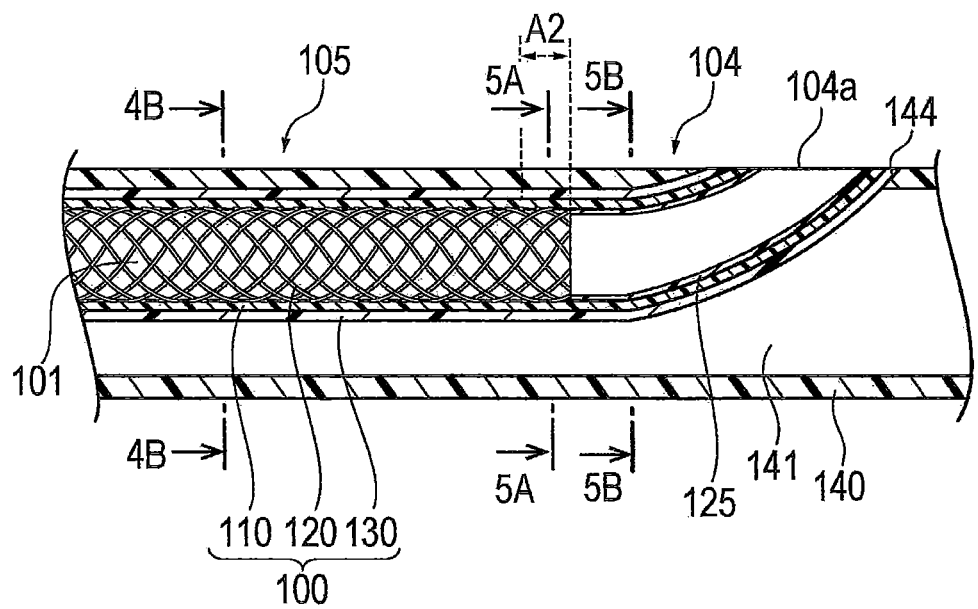
FIG. 2(B) is a view showing a longitudinal cross-section in an axial direction of a part of a dashed line portion 2B shown in FIG. 1.

FIG. 2(A) is an enlarged cross-sectional view showing a part of a dashed line portion 2A shown in FIG. 1, and FIG. 2(B) is an enlarged cross-sectional view of a part of a dashed line portion 2B shown in FIG. 1.

The balloon catheter 1 is a so-called rapid exchange type provided with a proximal opening portion 104a through which a guide wire W is guided out to be closer to the distal portion side of the shaft 10.

As shown in FIGS. 2(A) and 2(B), the shaft 10 comprises an inner tube 100 provided with a guide wire lumen 101 through which a guide wire W is inserted and an outer tube 140 that forms a pressurizing medium lumen 141 through which the pressurizing medium can circulate between the inner tube 100 and the outer tube 140.

The shaft 10 has a double tube structure in which the inner tube 100 is interpolated into or positioned inside the outer tube 140, and the inner tube 100 and the outer tube 140 are concentrically arranged.

As shown in FIG. 2(B), the inner tube 100 is provided with two opening portions, including a distal opening portion 103a at the distal end the inner tube 100 and a proximal opening portion 104a at the proximal end of the inner tube 100. The guide wire lumen 101 extends inside the inner tube 100 and communicates with the two opening portions 103a and 104a.

The inner tube 100 is configured of a hollow tubular material, and the proximal side or proximal end portion of the inner tube is curved outward in a radial direction as shown in FIG. 2(B).

A distal portion of the balloon 5 is bonded in vicinity of a distal end of the inner tube 100 in a liquid-tight and airtight manner by a known method of adhesion or the like. In addition, a portion of the inner tube 100 in the vicinity of the proximal end of the inner tube 100 is bonded, in a liquid tight and airtight manner, to a connecting opening portion 144 formed at a predetermined position of the outer tube 140. The guide wire W is inserted through the guide wire lumen 101 with the distal opening portion 103a provided at the distal end of the inner tube 100, as an entrance, and with the proximal opening portion 104a provided at the proximal end of the inner tube 100, as an exit.

The inner tube 100 is provided with a radiopaque contrast mark 170 representing a center position of the balloon 5 in the axial direction (i.e., the axial center of the balloon). For example, the radiopaque contrast mark 170 is formed by using a fine metal line having a small diameter which is made of a radiopaque material such as metal such as platinum, gold, silver, titanium, or tungsten or an alloy thereof. The radiopaque contrast mark 170 may be formed by using a resin material including powder of the radiopaque material.

The distal tip 150 is attached to the distal end of the inner tube 100. The distal tip 150 has a tapered shape having an outer diameter decreasing toward the distal side (distal end). The distal tip 150 has a through-hole 151 penetrating the distal tip 150 in an axial direction of the distal tip 150. The through-hole 151 enables the guide wire W inserted through the guide wire lumen 101 of the inner tube 100 to be pulled outside or pass to the outside of the inner tube 100.

For example, the distal tip 150 can be configured of a flexible resin member having a heat-shrinkable property. However, the material of the distal tip 150 is not particularly limited as long as the distal tip can be fixed to the inner tube 100. In a case where the distal tip 150 is configured of a resin member, the distal tip 150 can be fixed to the inner tube 100 by fusion. As shown in FIG. 2(A), the distal tip 150 may be fixed in a state in which a proximal surface of the distal tip 150 is in direct contact with the distal surface of the inner tube 100 and in a state in which an outer circumference of the proximal end of the distal tip 150 is covered by a distal end of the balloon 5. However, the fixation of the distal tip 150 is not limited in this manner. For example, the distal tip 150 may be fixed in a state of covering an outer circumference of the distal end of the inner tube 100 or may be fixed in a state of being inserted into the distal end of the inner tube 100.

The outer tube 140 is configured as a tubular member including a lumen extending from the vicinity of the proximal portion of the balloon 5 to the hub 160. A proximal portion of the balloon 5 is bonded in the vicinity of a distal end of the outer tube 140 in a liquid-tight and airtight manner by a known method of adhesion or the like.

Examples of constituent materials of the outer tube 140 include polyolefin such as polyethylene, polypropylene, an ethylene-propylene copolymer, or an ethylene-vinyl acetate copolymer, a thermoplastic resin such as soft polyvinyl chloride, various types of rubber such as silicone rubber or latex rubber, various types of elastomers such as a polyurethane elastomer, a polyamide elastomer, or a polyester elastomer, and crystalline plastics such as a polyamide, crystalline polyethylene, or crystalline polypropylene. For example, it is possible to compound an antithrombotic substance such as heparin, prostaglandin, urokinase, or an arginine derivative with such substances described above and to obtain a material having antithromboticity.

As shown in FIG. 1, the hub 160 is provided with a port 161 that is connectable to a supply device such as an in/deflator for supplying a pressurizing medium in a liquid-tight and airtight manner. For example, the port 161 of the hub 160 can be configured of a known luer taper or the like which is configured such that a fluid tube or the like is connectable or separable.

The pressurizing medium (for example, a physiological salt solution or a contrast agent) that is used for dilating the balloon 5 can flow into the shaft 10 via the port 161 of the hub 160. The pressurizing medium is supplied to the balloon 5 through the pressurizing medium lumen 141.

As shown in FIG. 2(A), the balloon 5 includes an intermediately located straight dilation effecting portion (pressurizing portion), which widens along with dilation deformation, a stenosed site formed in a body lumen, and tapered portions provided at both of the distal side and the proximal side of the dilation effecting portion. The distal portion of the balloon 5 is fixed to an outer surface of the inner tube 100 on the distal side. The proximal portion of the balloon 5 is fixed to an outer surface of the outer tube 140 on the proximal side.

Constituent materials of the balloon 5 are not particularly limited, and examples thereof include polyolefin such as polyethylene, polypropylene, or an ethylene-propylene copolymer, polyester such as polyethylene terephthalate, a thermoplastic resin such as polyvinyl chloride, an ethylene-vinyl acetate copolymer, a crosslinked ethylene-vinyl acetate copolymer, or polyurethane, polyamide, a polyamide elastomer, a polystyrene elastomer, silicone rubber, latex rubber, and the like.

Next, a structure of the inner tube 100 will be described in detail.

As shown in FIGS. 2(A) and 2(B), the inner tube 100 includes a predetermined tubular body 110, a reinforcing member 120 disposed on an inner side of the tubular body 110, and an outer layer 130 disposed on an outer surface of the tubular body 110.

As shown in FIG. 2(A), the inner tube 100 has a first region 103 including the distal portion provided with the distal opening portion 103a and a second region 105 that is disposed closer to the proximal side than the first region 103 (i.e., the second region 105 is positioned proximal of the first region 103). In addition, as shown in FIG. 2(B), the inner tube 100 has a third region 104 that is disposed to be closer to the proximal side than the second region 105 (i.e., the third region 104 is positioned proximal of the second region 105).

The distal tip 150 is disposed in the first region 103. The proximal opening portion 104a of the inner tube 100 is disposed in the third region 104.

The tubular body 110 has a hollow tubular shape extending in the axial direction of the inner tube 100. Similar to the tubular body 110, the outer layer 130 has a hollow tubular shape extending in the axial direction of the inner tube 100.

The tubular body 110 is made of a predetermined first resin. In addition, linear bodies 121 constituting the reinforcing member 120 are made of a predetermined second resin having a melting point higher than that of the first resin forming the tubular body 110.

Figure 4A:
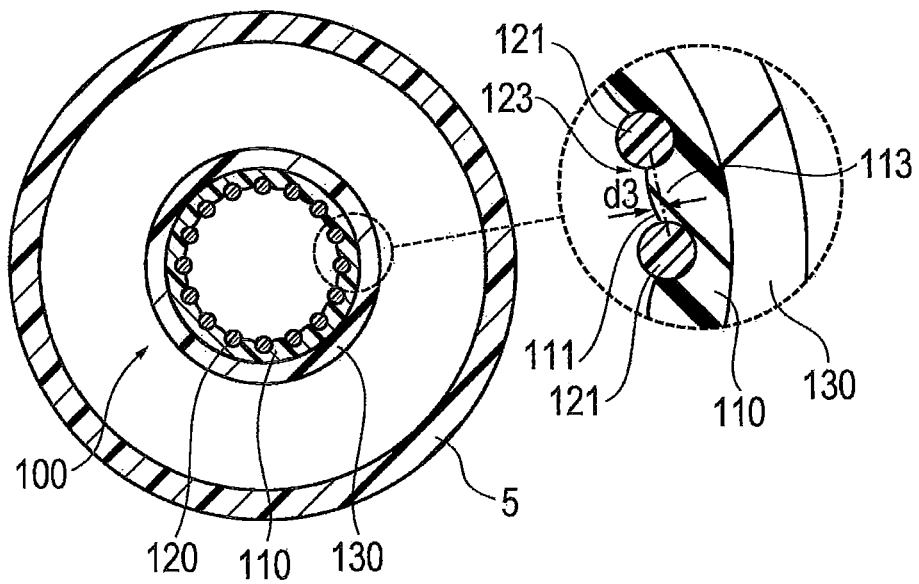
FIG. 4(A) is a view showing an axially orthogonal cross-section taken along the section line 4A-4A shown in FIG. 2(A)
Figure 4B:
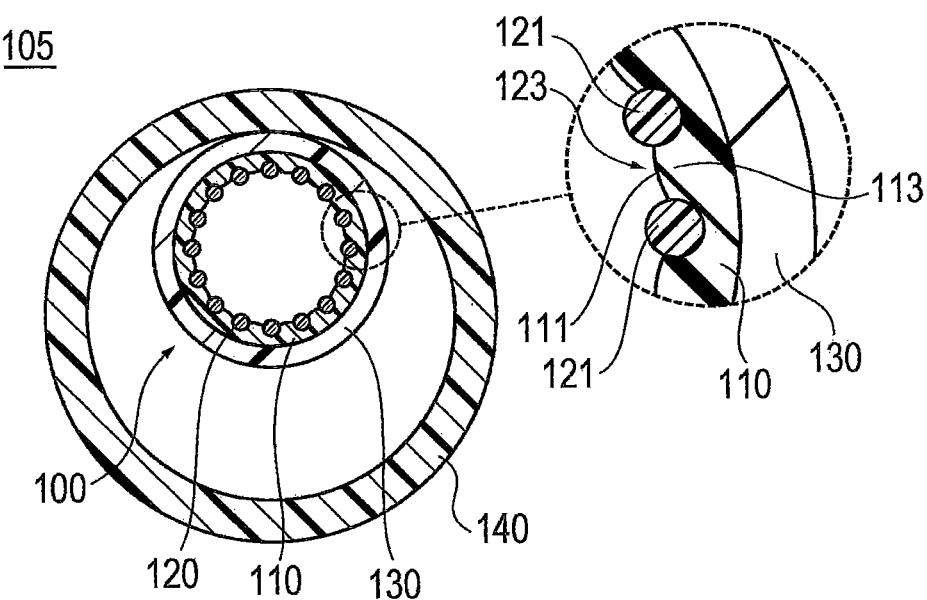
FIG. 4(B) is a view showing an axially orthogonal cross-section taken along the section line 4B-4B shown in FIG. 2(B).

As shown in FIG. 4(A), the tubular body 110 is provided with convex portions 113 on an inner surface 111 of the tubular body 110. The convex portions 113 each project from the inner surface 111 of the tubular body 110 toward an inner side in a radial direction (an inner side in a radiation direction) so as to penetrate respective gap portions 123 formed in the reinforcing member 120. The convex portions 113 thus project radially inward. In an example in the figures, axially orthogonal sections of the tubular body 110, the reinforcing member 120, and the outer layer 130 have a circular shape; however, the shape is not limited to the circular shape. For example, the cross section may have an elliptical shape, a rectangular shape, or the like.

The convex portions 113 are formed when a part of the first resin of the tubular body 110 is melted and flows into the gap portions 123. A cross-sectional shape of the convex portions 113 shown in the figures is an example of the convex shape, and the shape of the convex portions 113 can be appropriately modified.

As shown in FIG. 4(A), the reinforcing member 120 may be formed of a plurality of linear bodies 121 which are braided. The reinforcing member 120 is provided with the gap portions 123 formed between the plurality of linear bodies 121. In addition, the reinforcing member 120 has a tubular shape extending in the axial direction of the inner tube 100.

The reinforcing member 120 may have a function of increasing the kink resistance or the tensile strength of the inner tube 100 and a function of decreasing the sliding resistance of the guide wire W that is inserted through the guide wire lumen 101 of the inner tube 100. A contact area between the inner surface 111 of the tubular body 110 and the guide wire W is decreased in a site in which the linear bodies 121 constituting the reinforcing member 120 project from the inner surface 111 of the tubular body 110, and thus the sliding resistance is decreased.

For example, a one-over one-under structure in which the linear bodies 121 intersect with each other can be employed as a braid structure of the reinforcing member 120. However, the braid structure is not limited to such a structure.

For example, the linear body 121 can be formed of a wire having a circular cross-sectional shape. It is possible to decrease a contact area between the reinforcing member 120 and the guide wire W that is inserted through the guide wire lumen 101 of the inner tube 100 by using a circular wire, and thus it is possible to more suitably decrease the sliding resistance. In addition, the linear body 121 can be formed of a wire having an elliptical cross-sectional shape, for example. When the elliptical wires are used, an area of a site in which the wires overlap each other is increased. Therefore, it is possible to increase the rigidity of the reinforcing member 120. The reinforcing member 120 can also be formed of wires having a rectangular cross-sectional shape, may be formed by combining the circular, elliptical, and rectangular wires, or can be configured of wires having a shape other than the exemplified cross-sectional shapes. An outer diameter or the like of the used wire is not particularly limited.

The reinforcing member 120 is made of the second resin having the melting point higher than that of the first resin of the tubular body 110. When the reinforcing member 120 and the tubular body 110 are fused together, a part of the tubular body 110 is melted, whereas melting of the reinforcing member 120 is suppressed. Therefore, the shape of the linear body 121 of the reinforcing member 120 may be maintained and does not change. For example, similar to the second region 105, the contact area between the guide wire W and the inner surface 111 of the tubular body 110 is decreased in a region in which the shape of the linear bodies 121 is maintained, and thus the sliding resistance is significantly decreased. In the second region 105, when the reinforcing member 120 and the tubular body 110 are fused together due to heating from the outer circumference of the tubular body 110, a part of the reinforcing member 120 on the side of the tubular body 110 may also be melted.

For example, it is possible to use modified polyethylene (melting point: about 128° C.) as the first resin of the tubular body 110.

It is possible to use, as examples of the second resin of the linear body 121, polypropylene (melting point: about 168° C.), nylon 12 (melting point: about 179° C.), nylon 6 (melting point: about 225° C.), or nylon 66 (melting point: about 265° C.). However, the second resin may be a resin having a melting point higher than that of the first resin of the tubular body 110, and it is possible to select any resin depending on a relationship with a material of the tubular body 110.

In this embodiment disclosed by way of example, the linear bodies 121 constituting the reinforcing member 120 are formed of only the second resin. Therefore, it is possible to prevent the reinforcing member 120 and the guide wire W from being scratched against each other when the guide wire W is inserted through the guide wire lumen 101, and it is possible to suitably prevent the guide wire W from being damaged or broken. In addition, regarding the inner tube 100, since the tubular body 110 and the linear bodies 121 are formed of only the resin when a molding process is performed by using a mold or the like, it is possible to adjust an outer diameter, thickness, hardness, or the like by using fluidity of the resin. Therefore, the inner tube 100 is also excellent in processability.

Similar to the linear bodies 121, the outer layer 130 may be made of a resin having a melting point higher than that of the first resin of the tubular body 110. For example, the resins exemplified as the resins of the linear bodies 121 can be used as the resin of the outer layer 130. However, so long as the resin of the outer layer 130 is a resin having a melting point higher or greater than that of the first resin of the tubular body 110, the resin of the outer layer 130 is not limited. Similar to the second resin of the linear body 121, it is possible to select any resin depending on a relationship with a material of the tubular body 110.

In the second region 105 of the inner tube 100, the contact area between the inner surface 111 of the tubular body 110 and the guide wire W is decreased, it is preferable that the shape of the convex portions 113 or the like is adjusted depending on the thickness of the linear bodies 121. For example, a length or dimension d3 (refer to FIG. 4(A)) of the convex portions 113 of a site penetrating the respective gap portions 123 can be less than twice the thickness of the linear body 121 on a cross-section perpendicular to the axial direction of the inner tube 100. Each of the convex portions 113 is a portion projecting from the inner surface 111 of the tubular body 100 in the radially inward direction to penetrate respective gap portions 123 formed in the reinforcing member 120. Thus, a length or dimension d3 is a length between the outer (end) surface of the convex portion 113 and the inner surface 111 of the tubular body 100. This is because of the following reasons.

Figure 6A:
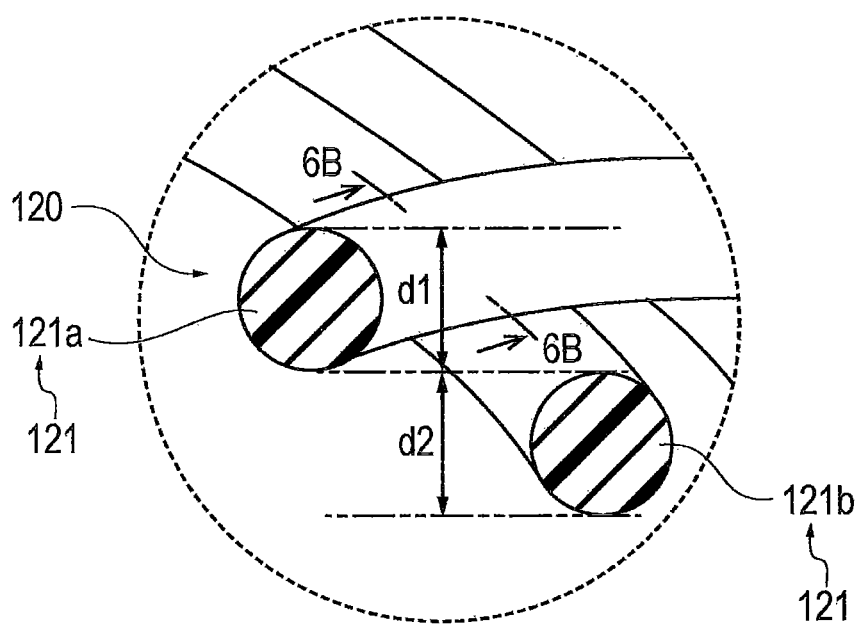
FIG. 6(A) is an enlarged view showing a part of a linear body constituting a reinforcing member.

As shown in FIG. 6(A), in a portion in which two linear bodies 121a and 121b overlap each other, the thickness of the reinforcing member 120 is the sum of dimensions of a thickness (outer diameter) d1 of the linear body 121a and a thickness (outer diameter) d2 of the linear body 121a. Hence, when the length or dimension d3 of the convex portion 113 of the site penetrating the gap portion 123 is less than the sum of the dimensions of both of the linear bodies 121a and 121b (less than twice the thickness of the linear body 121), it is possible to prevent the convex portion 113 from projecting to the inner side in the radial direction more than the gap portion 123 (i.e., the convex portion 113 does not project radially inwardly beyond the inner surface of the reinforcing member 120 (the inner surface of the linear body 121), and it is possible to suitably decrease the sliding resistance of the guide wire W. Similarly, even when the linear bodies 121 have a cross-sectional shape other than the circular cross-sectional shape, the length or dimension d3 of the convex portion 113 of the site penetrating the gap portion 123 is shorter than the total of the thickness dimensions of the braided sites, and thereby it is possible to suitably decrease the sliding resistance.

Figure 6B:
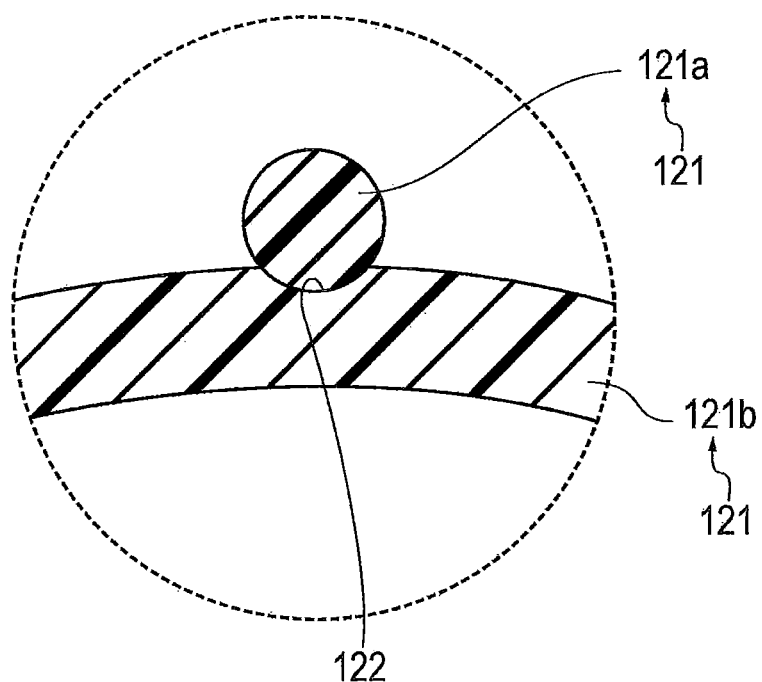
FIG. 6(B) is a view showing a cross-section taken along the section line 6B-6B shown in FIG. 6(A).

FIG. 6(B) is a view showing a cross-section of a site in which adjacent linear bodies 121a and 121b intersect with each other (a cross-sectional view taken along line 6B-6B shown in FIG. 6(A)). In the site in which the plurality of linear bodies 121a and 121b intersect with each other, at least one linear body 121b has a recessed shape. When heat is applied in order to fuse the tubular body 110 and the reinforcing member 120 in a state in which the linear bodies 121a and 121b are braided with each other, stress is concentrated on a contact site, and a concave portion 122 is formed by receiving an influence of the heat. When the concave portion 122 is formed, the linear bodies 121a and 121b are strongly caught on each other or held against each other. Therefore, it is possible to still better maintain the tubular shape of the reinforcing member 120, and thus it is possible to enhance a reinforcing function. Note that FIG. 6(B) shows an example in which the concave portion 122 is formed only on the one adjacent linear body 121b; however, the concave portion 122 may be formed on both of the linear bodies 121a and 121b depending on an applying state of the heat or an applying state of stress or may be formed only on the linear body 121a disposed on the side of the outer surface of the inner tube 100. In addition, since it is possible to appropriately change a depth, a shape, or the like of the concave portion 122 depending on a condition or the like during the fusion, the shape of the portion 122 is not limited to the shape shown in the figure. In addition, the linear bodies 121a and 121b are disposed to be orthogonal to each other; however, the disposition is not limited to such disposition, and it is possible to appropriately change an angle of the site (intersecting site) in which the linear bodies 121 overlap each other.

Next, a state of the linear bodies 121 in every portion of the inner tube 100 will be described.

Figure 3A:
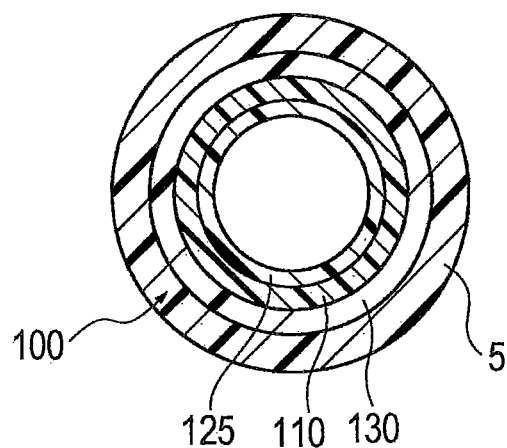
FIG. 3(A) is a view showing an axially orthogonal cross-section taken along the section line 3A-3A shown in FIG. 2(A)

FIG. 3(A) shows an axially orthogonal cross-section of the inner tube 100 in the first region 103. FIGS. 3(B), 4(A), 4(B), and 5(A) show an axially orthogonal cross-section of the inner tube 100 in the second region 105. FIG. 5(B) shows an axially orthogonal cross-section of the inner tube 100 in the third region 104. Note that a part of the configuration is enlarged and shown in the figures (a site surrounded in a dashed-line in the figures).

As shown in the figures, the linear bodies 121 project from the inner surface 111 of the tubular body 110 in the second region 105. In addition, the linear bodies 121 project from the inner surface 111 of the tubular body 110 in the first region 103 less than in the second region 105. In addition, the linear bodies 121 project from the inner surface 111 of the tubular body 110 in the third region 104 less than in the second region 105. A reason for adjusting a projection length of the linear body 121 in every portion of the inner tube 100 is described.

As described above, the contact area between the inner surface 111 of the tubular body 110 and the guide wire W is decreased in the site in which the linear bodies 121 constituting the reinforcing member 120 project from the inner surface 111 of the tubular body 110, and thus the sliding resistance is decreased. In other words, the sliding resistance of the guide wire W is decreased in the second region 105.

On the other hand, the projection length of the linear bodies 121 is shorter in the first region 103 and the third region 104 than in the second region 105.

When an uneven shape formed of the linear bodies 121 is disposed in the vicinity of the distal opening portion 103a of the inner tube 100, and the guide wire W is inserted into the guide wire lumen 101, the guide wire W is likely to be caught on the linear bodies 121, smooth insertion is hindered, or there is possibility that the guide wire W will be folded or bent. Hence, the projection length of the linear bodies 121 from the inner surface 111 is decreased in the vicinity of the distal opening portion 103a. In other words, the first resin of the tubular body 110 and the second resin of the linear bodies 121 are more melt-solidified in the first region 103 than in the second region 105. Here, melt-solidifying means melting of at least a part of the first resin and at least a part of the second resin and solidifying of the parts in a mixed state in which the first resin and the second resin are present together. Hence, the bonding strength of the tubular body 110 and the reinforcing member 120 in the first region 103 is higher than the bonding strength of the tubular body 110 and the reinforcing member 120 in the second region 105.

In addition, when an uneven shape formed of the linear bodies 121 is disposed in the vicinity of the proximal opening portion 104a of the inner tube 100, and the guide wire W is pulled outside from the guide wire lumen 101, the guide wire W is likely to be caught on the linear bodies 121, the pulling-out work is hindered, or there is possibility that the guide wire W will be folded or bent. Hence, the projection length of the linear bodies 121 from the inner surface 111 is also shortened or reduced in the vicinity of the proximal opening portion 104a. In other words, the first resin of the tubular body 110 and the second resin of the linear bodies 121 are more melt-solidified in the third region 104 than in the second region 105. Therefore, the bonding strength of the tubular body 110 and the reinforcing member 120 in the third region 104 is higher than the bonding strength of the tubular body 110 and the reinforcing member 120 in the second region 105.

As shown in FIGS. 2(A), 2(B), 3(A), and 5(B), in the inner tube 100 according to the embodiment, the linear bodies 121 disposed in the first region 103 and the third region 104 are melted, and thereby a melted portion 125 is formed. The linear bodies 121 do not have their original shape in the melted portion 125. In addition, the melted portion 125 is fused with the tubular body 110. Therefore, the uneven shape and the gap portion 123 which are formed of the linear bodies 121 are almost not provided in the first region 103 and the third region 104. Hence, the inner surface 111 of the inner tube 100 is a smooth surface with less unevenness in a circumferential direction in the first region 103 and the third region 104 than in the second region 105.

As described above, the linear bodies 121 disposed in the first region 103 and the third region 104 are melted to the extent that the linear bodies do not have the original shape, and thereby, it is possible to suitably prevent a problem that the guide wire W is caught in the vicinity of the distal opening portion 103a and the proximal opening portion 104a from occurring. However, the projection length of the linear bodies 121 in the first region 103 and the third region 104 is not particularly limited as long as the projection length is shorter than in the second region 105, and it is possible to prevent the problem that the guide wire W is caught or the like from occurring.

Figure 3B:
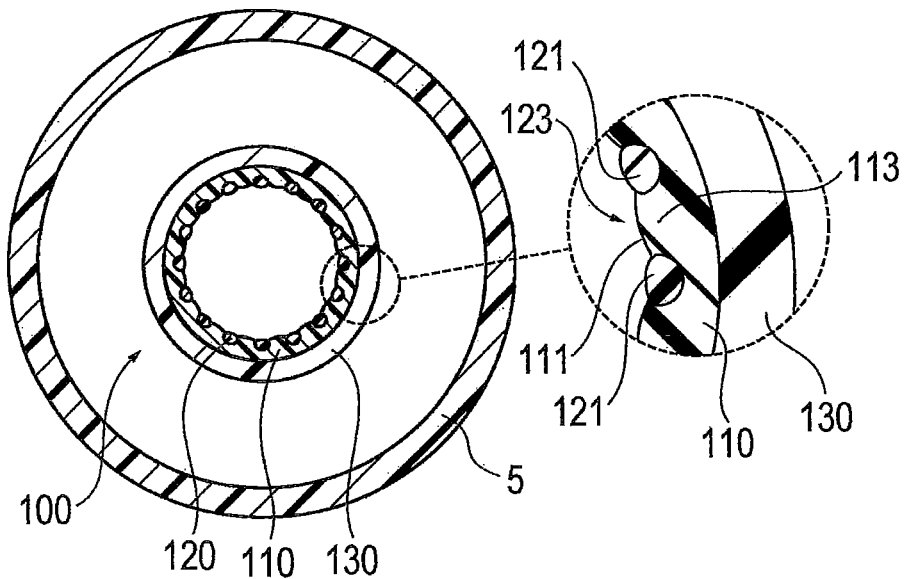
FIG. 3(B) is a view showing an axially orthogonal cross-section taken along the section line 3B-3B shown in FIG. 2(A).

As shown in FIGS. 2(A) and 3(B), the projection length of the linear body 121 from the inner surface 111 of the tubular body 110 is shortened from the second region 105 toward the first region 103 on a boundary portion or boundary region A1 between the first region 103 and the second region 105. As described above, the projection length of the linear bodies 121 is gradually shortened in the boundary portion A1. In this manner, a significant difference in physical properties between the first region 103 and the second region 105 due to the reinforcement of the reinforcing member 120 is suppressed, and thus the inner tube 100 is prevented from being folded or kinked in the vicinity of the boundary portion A1.

Figure 5A:
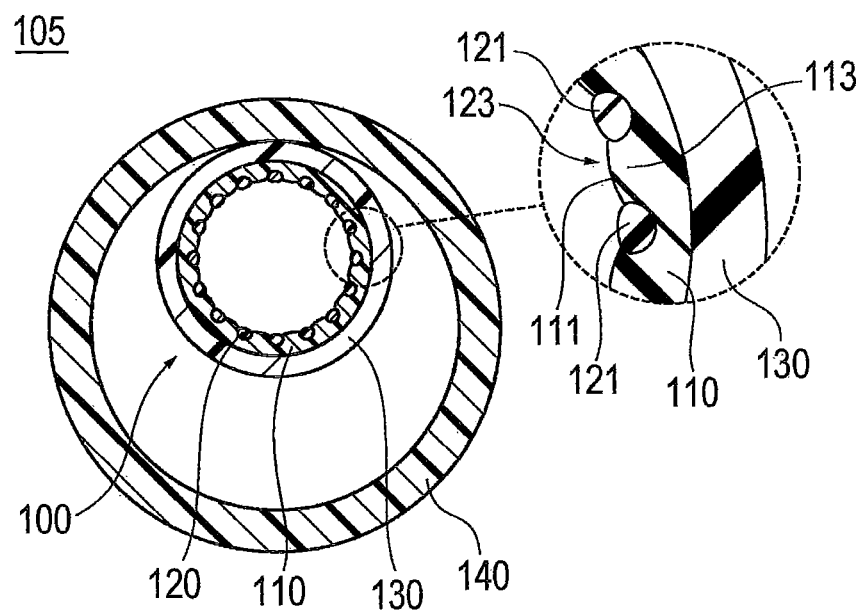
FIG. 5(A) is a view showing an axially orthogonal cross-section taken along the section line 5A-5A shown in FIG. 2(B)
Figure 5B:
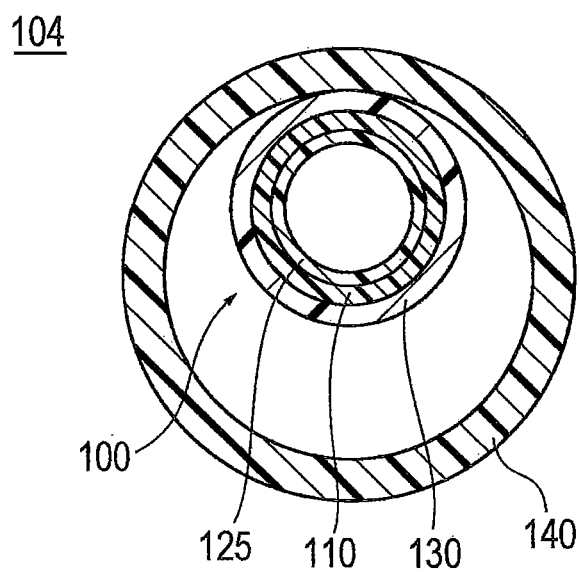
FIG. 5(B) is a view showing an axially orthogonal cross-section taken along the section line 5B-5B shown in FIG. 2(B).

As shown in FIGS. 2(B) and 5(A), the projection length of the linear body 121 from the inner surface 111 of the tubular body 110 is shortened from the second region 105 toward the third region 104 on a boundary portion A2 between the second region 105 and the third region 104. Similar to the boundary portion A1 between the first region 103 and the second region 105, the projection length of the linear bodies 121 is gradually shortened in the boundary portion or boundary region A2. In this manner, a significant difference in physical properties between the second region 105 and the third region 104 due to the reinforcement of the reinforcing member 120 is suppressed, and thus the inner tube 100 is prevented from being folded or kinked in the vicinity of the boundary portion A2.

Next, an operation of the balloon catheter 1 according to an embodiment disclosed by way of example will be described.

The balloon catheter 1 includes the outer tube 140 having a lumen, the inner tube 100 that is disposed in the lumen of the outer tube 140 and has the guide wire lumen 101 through which the guide wire W is insertable, and the balloon 5 whose distal end is fixed to the distal portion of the inner tube 100 and whose proximal end is fixed to the distal end of the outer tube 140. The proximal portion of the inner tube 100 is provided to form the proximal opening portion 104a that communicates with the guide wire lumen 101 in the middle of the outer tube 140. In other words, the inner tube 100 is located so that the proximal opening portion 104a is located at an intermediate part of the outer tube 100. The inner tube 100 has the tubular body 110 made of the first resin and the reinforcing member 120 disposed on the inner side of the tubular body 110. The reinforcing member 120 is configured of the linear bodies 121 made of the second resin. The inner tube 100 has the first region 103 including the distal portion provided with the distal opening portion 103a and the second region 105 that is disposed proximal of the first region 103. The linear bodies 121 project from the inner surface 111 of the tubular body 110 in the second region 105 and project less from the inner surface 111 of the tubular body 110 in the first region 103 than in the second region 105.

In addition, the balloon catheter 1 includes the outer tube 140 having the lumen, the inner tube 100 that is disposed in the lumen of the outer tube 140 and has the guide wire lumen 101 through which the guide wire W is insertable, and the balloon 5 fixed to the inner tube 100 on the distal side and the outer tube 140 on the distal side. The proximal portion of the inner tube 100 forms the proximal opening portion 104a that communicates with the guide wire lumen 101 in the middle of the outer tube 140. The inner tube 100 has the tubular body 110 made of the first resin and the reinforcing member 120 disposed on the inner side of the tubular body 110. The reinforcing member 120 is configured of the linear bodies 121 made of the second resin. The inner tube 100 has the first region 103 including the distal portion provided with the distal opening portion 103a and the second region 105 that is disposed proximal of the first region 103. The first resin of the tubular body 110 and the second resin of the linear bodies 121 are more melt-solidified in the first region 103 than in the second region 105.

The balloon catheter 1 configured as described above has the kink resistance or tensile strength improved by the reinforcing member 120 provided on the inner side of the tubular body 110 provided in the inner tube 100. In addition, in the inner tube 100 of the balloon catheter 1, the first resin and the second resin are melt-solidified in the first region 103 in the vicinity of the distal opening portion 103a. Therefore, the inner circumferential surface of the inner tube 100 in the first region 103 has little unevenness by the reinforcing member 120, and thus it is possible to prevent the guide wire W from being caught on the reinforcing member 120 in the vicinity of the distal opening portion 103a. On the other hand, the sliding resistance of the guide wire W due to the unevenness by the reinforcing member 120 is decreased in the second region 105 on the proximal side more than in the vicinity of the distal opening portion 103a. That is, the contact area between the guide wire W and the inner surface of the inner tube 100 is reduced by the unevenness formed by the reinforcing member 120 and so the sliding resistance of the guide wire W is decreased more in the second region 105 on the proximal side than in the vicinity of the distal opening portion 103a.

Since the tubular body 110 and the reinforcing member 120 both include the resin or are both made of resin, the tubular body 110 and the reinforcing member 120 are rather easily fused together, compared to a case where the reinforcing member 120 is formed of metal. Therefore, when an end portion of the inner tube 100 is cut and the distal tip 150 is attached, there is no need to perform an end-portion treatment for preventing dispersion of an end portion of the reinforcing member 120, and thus it is relatively easy to perform a manufacturing operation. Further, when a portion in the vicinity of the proximal end of the inner tube 100 is attached to a connecting opening portion 144 formed at a predetermined position of the outer tube 140, there is also no need to perform the end-portion treatment such that the end portion of the reinforcing member 120 is not dispersed, and thus it is rather easy to perform the manufacturing operation.

In addition, the distal tip 150 is disposed in the first region 103. Therefore, when the distal end of the balloon catheter 1 comes into contact with a biological organ (intravascular wall), it is possible to suitably prevent the biological organ from being damaged or the like.

In addition, the projection length of the linear body 121 from the inner surface 111 of the tubular body 110 is shortened from the second region 105 toward the first region 103 on the boundary portion or boundary region A1 between the first region 103 and the second region 105. Therefore, a significant difference in physical properties between the first region 103 and the second region 105 due to the reinforcement of the reinforcing member 120 is suppressed, and thus the inner tube 100 is prevented from being folded or kinked in the vicinity of the boundary portion A1.

In addition, the inner tube 100 has the third region 104 that is disposed proximal of the second region 105, and thus the linear bodies 121 project less from the inner surface 111 of the tubular body 110 in the third region 104 than in the second region 105. Therefore, when the guide wire W is pulled outside from the guide wire lumen 101 via the proximal opening portion 104a of the inner tube 100, it is possible to prevent the guide wire W from being caught on the linear bodies 121, and thus it is possible to more smoothly pull out the guide wire W.

In addition, the projection length of the linear body 112 from the inner surface 111 of the tubular body 110 is shortened or reduced from the second region 105 toward the third region 104 on the boundary portion or boundary region A2 between the second region 105 and the third region 104. The projection length of the linear body 112 is thus gradually reduced in the boundary portion A2 from the second region 105 toward the third region 104. Therefore, a significant difference in physical properties between the second region 105 and the third region 104 due to the reinforcement of the reinforcing member 120 is suppressed, and thus the inner tube 100 is prevented from being folded or kinked in the vicinity of the boundary portion A2.

In addition, the reinforcing member 120 is formed of the plurality of linear bodies 121 which are braided. Therefore, the inner tube 100 has good kink resistance or tensile strength by the reinforcing member 120.

In addition, the linear body 121 may be formed of a wire having a circular cross-sectional shape. In this manner, it is possible to decrease the contact area between the reinforcing member 120 and the guide wire W that is inserted through the guide wire lumen 101, and thus it is possible to more suitably decrease the sliding resistance.

In addition, the linear bodies 121 are formed of only the second resin. In this manner, it is possible to prevent the reinforcing member 120 and the guide wire W from scratching against each other when the guide wire W is inserted through the guide wire lumen 101, and it is possible to suitably prevent the guide wire W from being damaged or broken. Further, regarding the inner tube 100, since the tubular body 110 and the linear bodies 121 are formed of only the resin when a molding process is performed by using a mold or the like, it is possible to adjust the outer diameter, thickness, hardness, or the like by using the fluidity of the resin. Therefore, the inner tube 100 is also excellent in processability.

In addition, the outer layer 130 is configured or made of a resin having a melting point higher than the first resin and is disposed on the outer surface of the tubular body 110. In this manner, when heat is applied from the side of the outer layer 130, it is possible to suitably prevent the reinforcing member 120 from receiving an influence of the heat. Further, since it is possible to melt the tubular body 110 that is disposed on the outer layer of the reinforcing member 120 such that the reinforcing member 120 and the outer layer 130 are fused together, it is possible to bond the reinforcing member 120 to the outer layer 130 while the shape of the reinforcing member 120 is suitably prevented from being damaged even in a case where the melting point of the outer layer 130 approximates the melting point of the reinforcing member 120.

Modification Example 1

Next, an inner tube 200 according to Modification Example 1 of the first embodiment will be described with reference to FIGS. 7(A) and 7(B). In the following description of the modification example, features that are similar to those described above are identified by a common reference numeral and a detailed description of such features is not repeated.

Figure 7A:
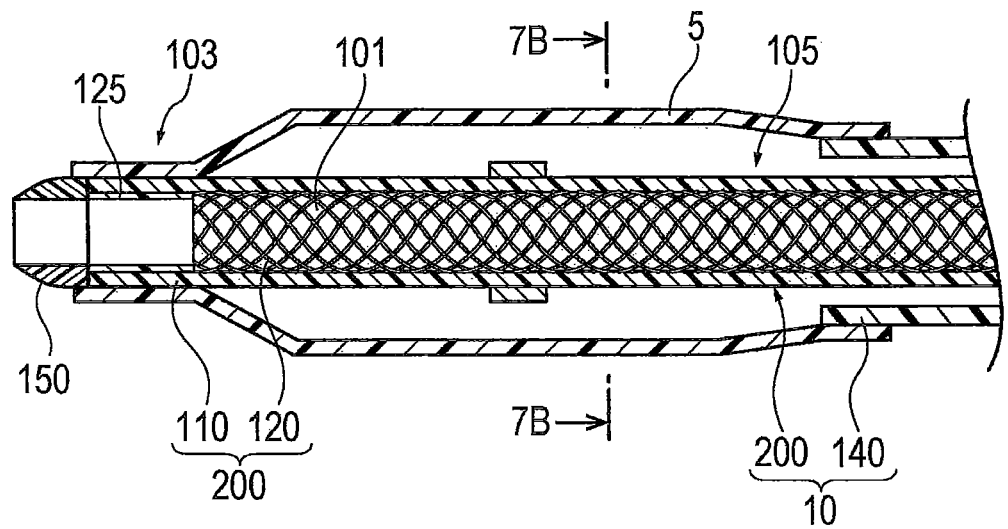
FIG. 7(A) is a view showing a longitudinal cross-section of a distal portion of a balloon catheter according to Modification Example 1 of the first embodiment.
Figure 7B:
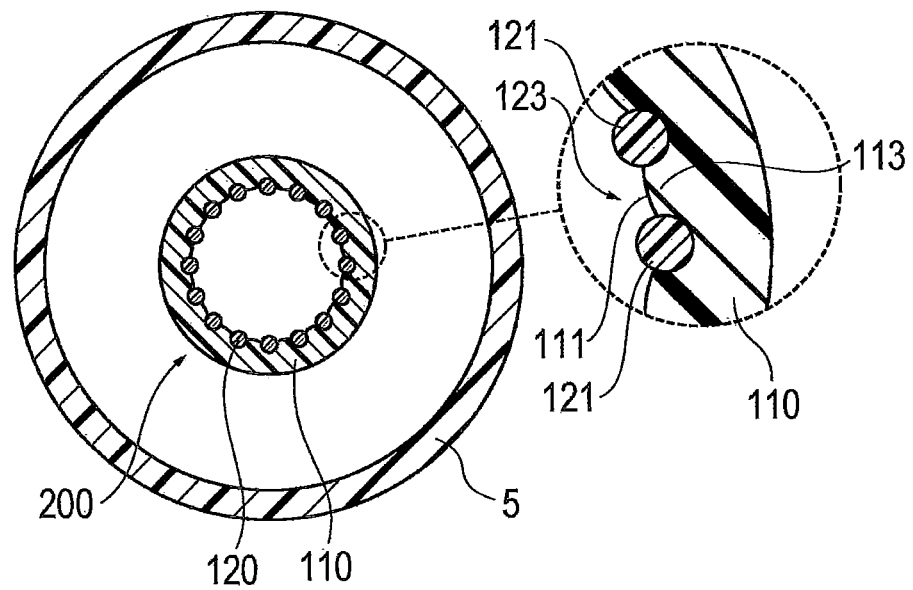
FIG. 7(B) is a view showing an axially orthogonal cross-section taken along the section line 7B-7B shown in FIG. 7(A).

As shown in FIGS. 7(A) and 7(B), the inner tube 100 may not include the outer layer 130. In other words, the inner tube 100 can be configured of only the tubular body 110 made of the first resin and the reinforcing member 120. Even in a case of such a configuration, the tubular body 110 and the reinforcing member 120 are fused together, and thereby it is possible to decrease the sliding resistance of the guide wire W. In addition, since it is possible to reduce the number of members to the extent that the outer layer 130 is not used, it is possible to achieve a decrease in manufacturing costs.

Modification Example 2

Next, a reinforcing member 320 according to Modification Example 2 of the first embodiment will be described with reference to FIG. 8. In the following description of the modification example 2, features that are similar to those described above are identified by a common reference numeral and a detailed description of such features is not repeated.

Figure 8:
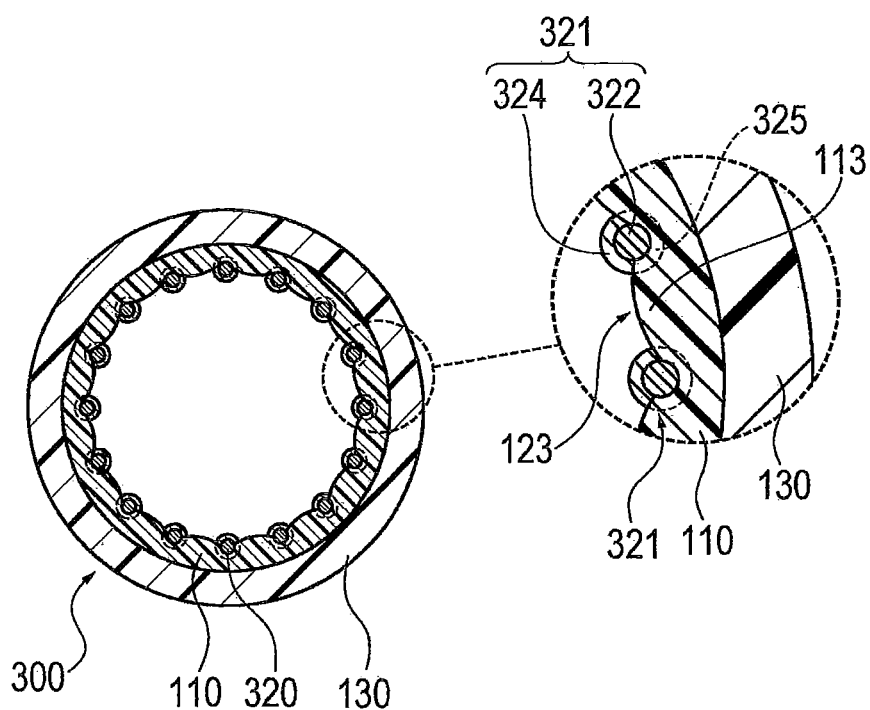
FIG. 8 is a view showing an axially orthogonal cross-section of an inner tube according to Modification Example 2 of the first embodiment.

As shown in FIG. 8, linear bodies 321 constituting the reinforcing member 320 can be configured to have a core material 322 made of metal and a second resin 324 that covers an outer circumferential surface of the core material 322, for example.

It is possible to use, as metal of the core material 322, various types of metal wires made of stainless steel, tungsten, copper, nickel, titanium, a piano wire, a cobalt-chromium based alloy, a nickel-tungsten based alloy (superelastic alloy), a copper-zinc based alloy, or an amorphous alloy.

It is possible to use, as an example of the second resin 324, a resin that is the same as the second resin that is used in the embodiment described above.

The use of the linear bodies 321 having the core material 322 made of metal enables an inner tube 300 to have still more improved tensile strength. In addition, as shown in FIG. 8, a part of the second resin 324 is melted, and a site 325, in which the second resin and the inner surface 111 of the tubular body 110 are fused together, is formed. In this manner, the bonding strength between the linear bodies 321 and the tubular body 110 is increased. In this manner, since the core material 322 is strongly fixed to the tubular body 110, it is possible to suitably prevent a problem that the core material 322 is dispersed or the like from occurring.

The linear body 321 having a circular cross-section is illustrated in FIG. 8; however, similarly, a linear body that is formed to have a cross-section with an elliptical or rectangular shape other than the circular shape can also be used as the core material 322.

As described above, the inventive balloon catheter disclosed here is described in the embodiment and the plurality of modification examples set forth above; however, the present invention is not limited to the configuration described in the embodiment and the modification examples, and it is possible to perform appropriate modifications within the scope of the claims.

For example, the reinforcing member can be configured of coil-shaped linear bodies. A configuration, in which the reinforcing member is configured of the coil-shaped linear bodies, enables the inner tube to have bendability.

As another example, the balloon catheter may be configured to be a balloon catheter that is called a so-called over-the-wire type formed to have a guide wire lumen extending from a distal end to a proximal end of a shaft. In a case of the over-the-wire type balloon catheter 1, the projection length of the linear bodies in the vicinity of the distal opening portion is adjusted to be more shortened than in the second region which is positioned on the proximal side, and thereby it is possible to suitably prevent the guide wire from being caught on the linear bodies when the guide wire W is inserted into the guide wire lumen.

In addition, the balloon catheter may have a configuration in which the linear bodies project from the inner surface of the tubular body at least in the second region and project less from the inner surface of the tubular body in the first region than in the second region. It is possible to modify a configuration or the like other than those described in the embodiment. For example, the linear bodies may not be melted in the third region, or the projection length of the linear bodies may not be adjusted based on a relationship with the first region or the second region.

Second Embodiment

Set forth below is a detailed description of a balloon catheter and a medical elongated body representing further examples of the inventive balloon catheter and medical elongated body disclosed here. The dimensional ratios in the drawing figures is enlarged depending on the description and the ratio may be different from an actual ratio in some cases.

Figure 9:
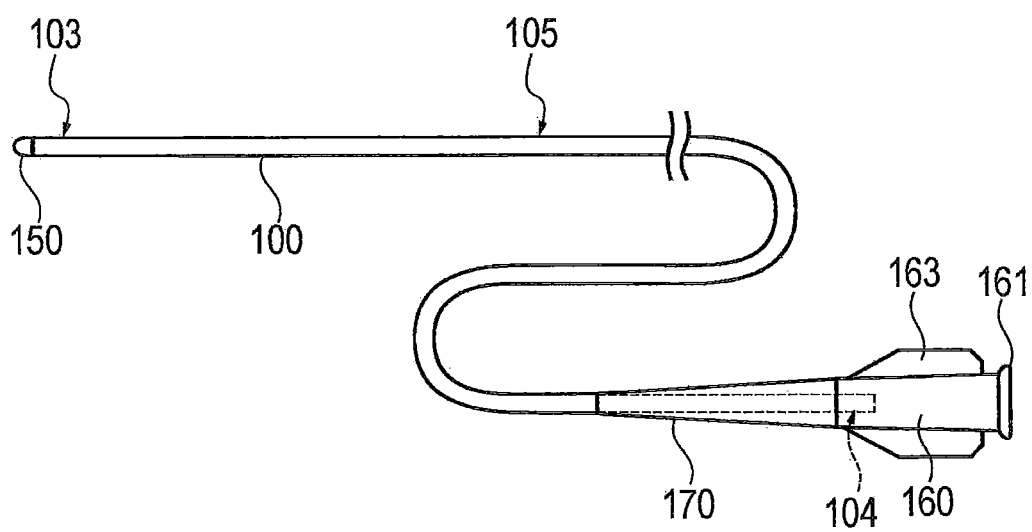
FIG. 9 is a view showing a medical elongated body according to a second embodiment.
Figure 10A:
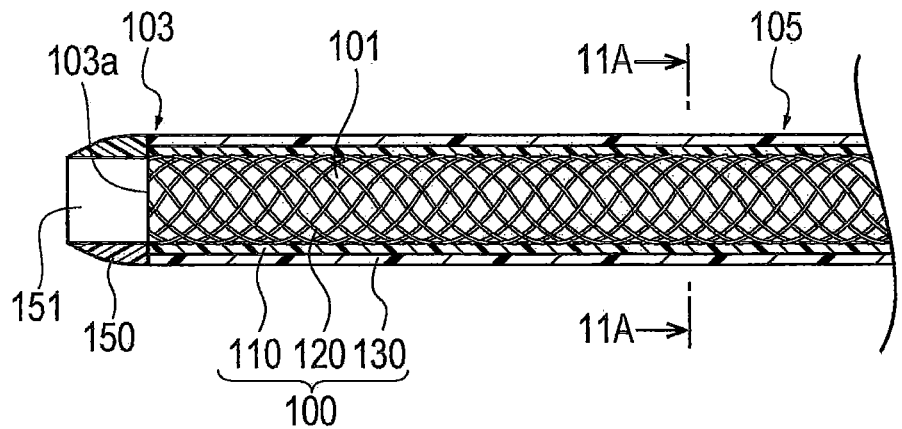
FIG. 10(A) is a view showing a longitudinal cross-section in an axial direction of a distal portion of the medical elongated body according to the second embodiment.
Figure 10B:
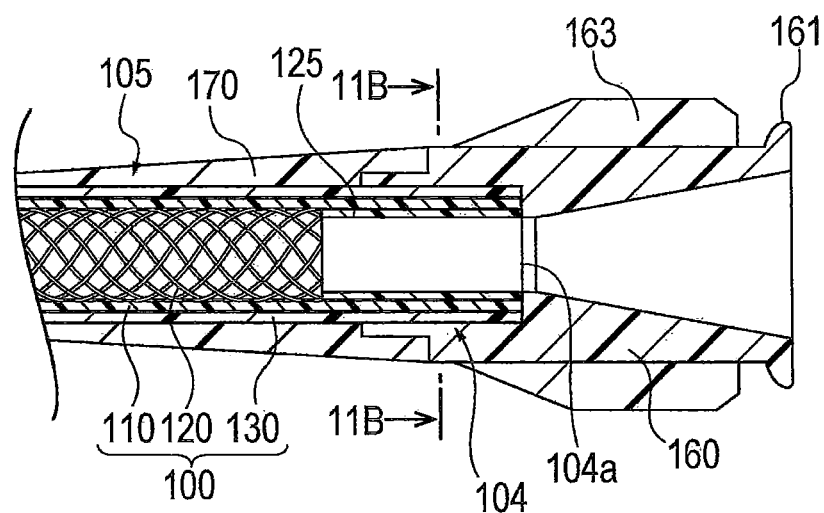
FIG. 10(B) is a view showing a longitudinal cross-section in an axial direction of a proximal portion of the medical elongated body according to the embodiment.
Figure 11A:
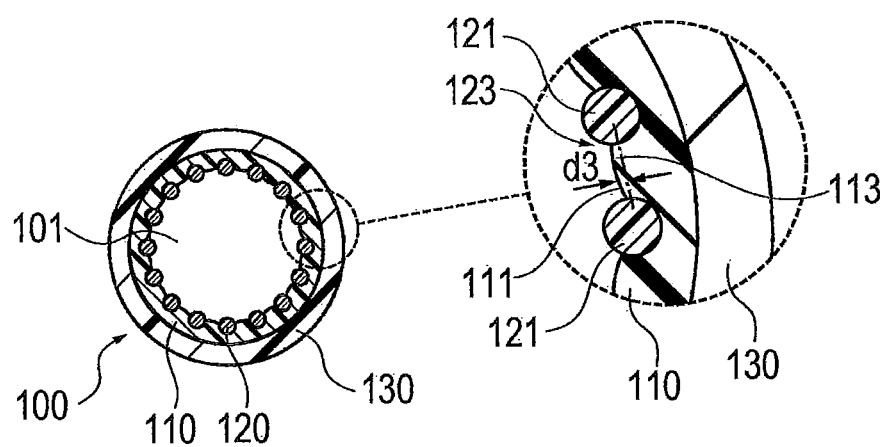
FIG. 11(A) is a view showing an axially orthogonal cross-section taken along the section line 11A-11A shown in FIG. 10(A)

FIGS. 9 to 11 are views showing a configuration of every portion of a medical elongated body according to the embodiment, and FIG. 11 is a view showing a configurational example of a linear body of a reinforcing member according to an embodiment. FIG. 11(A) is an enlarged view showing a part of the configuration (a site surrounded in a dashed-line in FIG. 11(A)).

With reference to FIG. 9, a medical elongated body 10 according to the embodiment is configured to be a catheter for performing a medical treatment, diagnosis, or the like by being inserted into a blood vessel, a bile duct, a trachea, an esophagus, a urethra, or another body lumen or a body-cavity.

As shown in FIG. 9, the medical elongated body 10 includes an elongated catheter main body 100 that can be guided into a living body, a distal tip 150 attached to a distal portion 103 of the catheter main body 100, and a hub 160 interlocked with a proximal portion 104 of the catheter main body 100. In addition, the medical elongated body 10 includes an anti-kink protector (strain relief) 170 in the vicinity of an interlock portion between the catheter main body 100 and the hub 160.

In the following description, a side on which the distal tip 150 is disposed in the catheter main body 100 is referred to as a distal side or distal end, a side on which the hub 160 is disposed in the catheter main body 100 is referred to as a proximal side or the proximal end, and a direction in which the catheter main body 100 extends is referred to as an axial direction.

FIG. 10(A) is an enlarged cross-sectional view showing the vicinity of the distal portion 103 of the medical elongated body 10, and FIG. 10(B) is an enlarged cross-sectional view showing the vicinity of the proximal portion 104 of the medical elongated body 10.

As shown in FIGS. 10(A) and 10(B), the catheter main body 100 is configured to be a flexible tubular member provided with a lumen 101 extending in the axial direction, a distal opening portion 103a that communicates with the lumen 101, and the proximal opening portion 104a that communicates with the lumen 101.

The catheter main body 100 comprises a tubular body 110, a reinforcing member 120 (refer to FIG. 11(A)) that is disposed on an inner surface 111 of the tubular body 110, which forms the lumen 101 of the catheter main body 100, and an outer layer 130 disposed on the outer surface of the tubular body 110.

The tubular body 110 has a hollow tubular shape extending in the axial direction of the catheter main body 100. Similar to the tubular body 110, the outer layer 130 has a hollow tubular shape extending in the axial direction of the catheter main body 100.

Figure 12A:
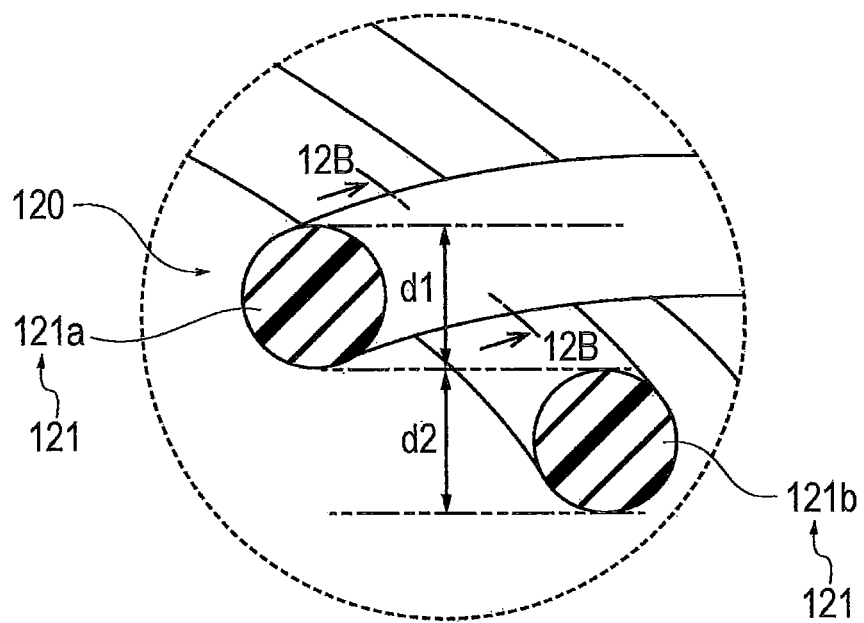
FIG. 12(A) is an enlarged view showing a part of a linear body constituting a reinforcing member.

As shown in FIGS. 11(A) and 12(A), the reinforcing member 120 is formed of the plurality of linear bodies 121 which are braided. The reinforcing member 120 is provided with a gap portion 123 formed between the plurality of linear bodies 121. The reinforcing member 120 has a tubular shape extending in the axial direction of the catheter main body 100.

The distal tip 150 attached to the catheter main body 100 has a tapered shape having an outer diameter decreasing toward the distal side or distal end. The distal tip 150 has a through-hole 151 penetrating the distal tip 150 in an axial direction of the distal tip 150. The through-hole 151 can guide the medical device such as the guide wire or the like, which is inserted through the lumen 101 of the catheter main body 100, to the outside of the catheter main body 100.

For example, the distal tip 150 can be configured of a flexible resin member having a heat-shrinkable property. However, the material of the distal tip 150 is not particularly limited as long as the distal tip can be fixed to the catheter main body 100. In a case where the distal tip 150 is configured or made of a resin member, the distal tip 150 can be fixed to the catheter main body 100 by fusion. As shown in FIG. 10(A), the distal tip 150 is fixed in a state in which a proximal surface thereof is in direct contact with a distal surface of the catheter main body 100. However, the fixation of the distal tip 150 is not limited in this way. For example, the distal tip 150 may be fixed in a state of covering an outer circumference of the distal end of the catheter main body 100 or may be fixed in a state of being inserted into the inner side of the distal end of the catheter main body 100.

The hub 160 is provided with a port 161 functioning as an insertion opening through which the medical device such as the guide wire is inserted into the lumen 101 of the catheter main body 100 and a wing portion 163 that is used for checking an orientation or the like when the medical elongated body 10 is operated. The hub 160 can be attached to cover an outer circumference of the proximal portion 104 of the catheter main body 100 by using an adhesive or a fixture. It is possible to use, as examples of constituent materials of the hub 160, a thermoplastic resin such as polycarbonate, polyamide, polysulfone, or polyarylate.

Next, a structure of the catheter main body 100 will be described.

As shown in FIG. 11(A), the tubular body 110 is provided with convex portions 113 formed on the inner surface 111 of the tubular body 110. The convex portions 113 project from the inner surface 111 toward an inner side in a radial direction (an inner side in a radiation direction) so as to penetrate the respective gap portions 123 formed in the reinforcing member 120. The convex portions 113 thus project radially inward. In an example in the figures, axially orthogonal cross-sections of the tubular body 110, the reinforcing member 120, and the outer layer 130 have a circular shape; however, the shape is not limited to the circular shape. For example, the cross-section may have an elliptical shape, a rectangular shape, or the like.

The tubular body 110 is made of the predetermined first resin. In addition, the linear bodies 121 are made of the predetermined second resin. The melting point of the first resin is lower than the melting point of the second resin. As shown in FIG. 11(A), the first resin of the tubular body 110 is fused with the second resin in a state in which the convex portion 113 penetrates the gap portion (mesh) 123 constituting the reinforcing member 120.

The convex portions 113 are formed when a part of the first resin of the tubular body 110 is melted and flows into the respective gap portions 123. A cross-sectional shape of the convex portions 113 shown in the figures is an example, and the shape of the convex portions 113 can be appropriately modified.

The reinforcing member 120 has a function of increasing the kink resistance or the tensile strength of the catheter main body 100 and a function of decreasing the sliding resistance of the various types of medical devices that are inserted through the lumen 101 of the catheter main body 100. In addition, in the embodiment, in order to suitably exhibit the function of decreasing the sliding resistance, the reinforcing member 120 is formed of a resin having a melting point higher than the first resin of the tubular body 110. When the reinforcing member 120 and the tubular body 110 are fused together, a part of the tubular body 110 is melted, whereas melting of the reinforcing member 120 is suppressed. Therefore, the shape of the linear body 121 of the reinforcing member 120 is maintained. Since a contact area between the medical device and the inner surface 111 of the tubular body 110 is decreased in a region in which the shape of the linear bodies 121 is maintained, and thus the sliding resistance is significantly decreased. When the reinforcing member 120 and the tubular body 110 are fused together due to heating from the outer circumference of the tubular body 110, a part of the reinforcing member 120 on the side of the tubular body 110 may be melted.

For example, a one-over one-under structure in which the linear bodies 121 intersect with each other can be employed as a braid structure of the reinforcing member 120. However, the structure is not limited to such a one-over one-under structure.

For example, the linear body 121 can be formed of a wire having a circular cross-sectional shape. It is possible to decrease a contact area between the reinforcing member 120 and the medical device that is inserted through the lumen 101 of the catheter main body 100 by using a wire having a circular cross-section, and thus it is possible to more appropriately decrease the sliding resistance. In addition, the linear body 121 can be formed of a wire having an elliptical cross-sectional shape, for example. When the elliptical wires are used, an area of a site in which the wires overlap each other is increased. Therefore, it is possible to increase the stiffness of the reinforcing member 120. Note that the reinforcing member 120 can also be formed of wires having a rectangular cross-sectional shape, may be formed by combining the circular, elliptical, and rectangular wires, or can be configured of wires having a cross-section shape other than the exemplified cross-sectional shapes, for example. An outer diameter or the like of the used wire is not particularly limited.

For example, it is possible to use modified polyethylene (melting point: about 128° C.) as the first resin of the tubular body 110.

It is possible to use, as examples of the second resin of the linear body 121, polypropylene (melting point: about 168° C.), nylon 12 (melting point: about 179° C.), nylon 6 (melting point: about 225° C.), or nylon 66 (melting point: about 265° C.). However, the second resin may be a resin having a melting point higher than that of the first resin of the tubular body 110, and it is possible to select any resin depending on a relationship with a material of the tubular body 110.

In the embodiment, since the linear bodies 121 constituting the reinforcing member 120 are formed of only the second resin, it is possible to prevent the reinforcing member 120 and the guide wire from scratching against each other when the metal medical device such as the guide wire is inserted through the lumen 101 of the catheter main body 100, and it is possible to suitably prevent the guide wire from being damaged or broken. In addition, regarding the catheter main body 100, since the tubular body 110 and the linear bodies 121 are formed of only the resin when a molding process is performed by using a mold or the like, it is possible to adjust an outer diameter, thickness, hardness, or the like by using fluidity of the resin. Therefore, the catheter main body 100 is also excellent in processability.

Similar to the linear bodies 121, the outer layer 130 is made of a resin having the melting point higher than that of the first resin of the tubular body 110. For example, the resins exemplified as the resins of the linear bodies 121 can be used as the resin of the outer layer 130. However, so long as the resin of the outer layer 130 is a resin having a melting point higher or greater than that of the first resin of the tubular body 110, the resin of the outer layer 130 is not limited. Similar to the second resin of the linear body 121, it is possible to select any resin depending on a relationship with a material of the tubular body 110.

In order to decrease the contact area between the inner surface 111 of the tubular body 110 and the medical device, it is preferable that the shape of the convex portions 113 or the like is adjusted depending on the thickness of the linear bodies 121. For example, a length d3 or dimension (refer to FIG. 11(A)) of the convex portion 113 of a site penetrating the gap portion 123 can be less than twice the thickness of the linear body 121 on a cross-section perpendicular to the axial direction of the catheter main body 100. This is because of the following reasons.

As shown in FIG. 12(A), in a portion in which two linear bodies 121a and 121b overlap each other, the thickness of the reinforcing member 120 is the sum of dimensions of a thickness (outer diameter) d1 of the linear body 121a and a thickness (outer diameter) d2 of the linear body 121a. Hence, when the length or dimension d3 of the convex portion 113 of the site penetrating the gap portion 123 is less than the sum of the dimensions of both of the linear bodies 121a and 121b (less than twice the thickness of the linear body 121), it is possible to prevent the convex portions 113 from projecting to the inner side in the radial direction more than the respective gap portion 123, and it is possible to suitably decrease the sliding resistance that acts between the medical device and the inner surface 111 of the tubular body 110. Similarly, even when the linear bodies 121 have a cross-sectional shape other than the circular cross-sectional shape, the length or dimension d3 of the convex portion 113 of the site penetrating the gap portion 123 is shorter than the total of the thickness dimensions of the braided sites, and thereby it is possible to suitably decrease the sliding resistance.

Figure 12B:
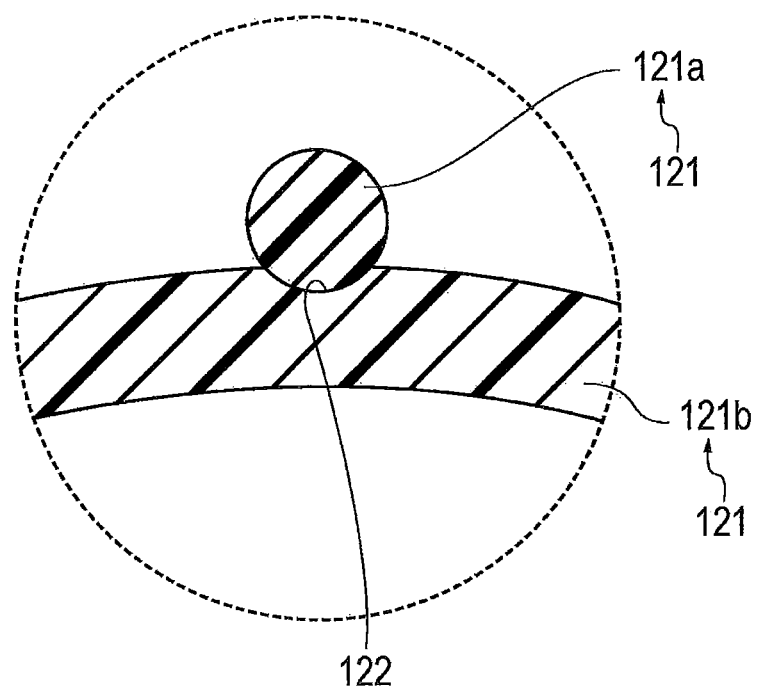
FIG. 12(B) is a view showing a cross-section taken along the section line 12B-12B shown in FIG. 12(A).

FIG. 12(B) is a view showing a cross-section of a site in which adjacent linear bodies 121a and 121b intersect with each other (a cross-sectional view taken along line 12B-12B shown in FIG. 12(A)). In the site in which the plurality of linear bodies 121a and 121b intersect with each other, at least one linear body 121b has a recessed shape. When heat is applied in order to fuse the tubular body 110 and the reinforcing member 120 in a state in which the linear bodies 121a and 121b are braided with each other, stress is concentrated on a contact site, and a concave portion 122 is formed by receiving an influence of the heat. When the concave portion 122 is formed, the linear bodies 121a and 121b are strongly caught on each other. Therefore, it is possible to still better maintain the tubular shape of the reinforcing member 120, and thus it is possible to enhance a reinforcing function. FIG. 12(B) shows an example in which the concave portion 122 is formed only on the one adjacent linear body 121b; however, the concave portion 122 may be formed on both of the linear bodies 121a and 121b depending on an applying state of the heat or an applying state of stress or may be formed only on the linear body 121a disposed on the side of the outer surface of the catheter main body 100. In addition, since it is possible to appropriately change a depth, a shape, or the like of the concave portion 122 depending on a condition or the like during the fusion, the shape thereof is not limited to the shape shown in the figure. In addition, the linear bodies 121a and 121b are disposed to be orthogonal to each other; however, the disposition is not limited to such disposition, and it is possible to appropriately change an angle of the site (intersecting site) in which the linear bodies 121 overlap each other.

Figure 11B:
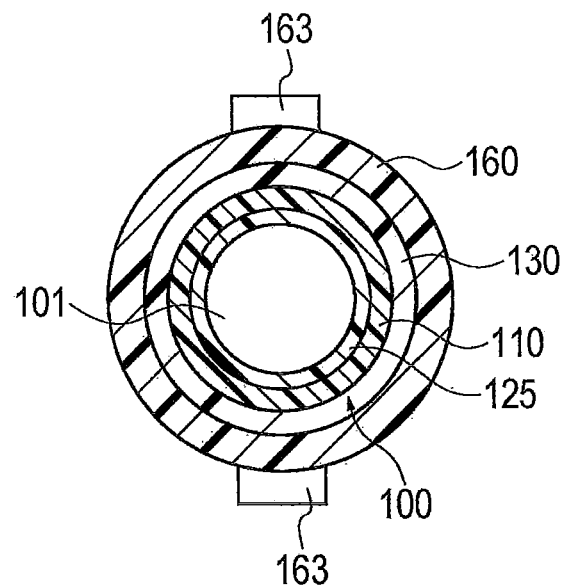
FIG. 11(B) is a view showing an axially orthogonal cross-section taken along the section line 11B-11B shown in FIG. 10(B).

As shown in FIGS. 10(A), and 10(B), the catheter main body 100 has an intermediate portion 105 extending between the distal portion 103 provided with the distal tip 150 and the proximal portion 104 provided with the hub 160. In addition, as shown in FIG. 11(A), the linear bodies 121 project from the inner surface 111 of the tubular body 110 in the intermediate portion 105. On the other hand, as shown in FIG. 11(B), the linear bodies 121 project less from the inner surface 111 of the tubular body 110 in the proximal portion 104 than in the intermediate portion 105. A reason for adjusting a projection length of the linear body 121 in every portion of the catheter main body 100 is as follows.

The proximal portion 104 of the catheter main body 100 is provided with the proximal opening portion 104a which is an entrance used when the medical device is inserted into the lumen 101 of the catheter main body 100. For example, when a recessed shape formed of the linear bodies 121 is disposed in the vicinity of the proximal opening portion 104a, and the medical device is inserted into the lumen 101, a problem can arise in that the medical device is likely to be caught on the linear bodies 121, smooth insertion is hindered, or the medical device is likely to become damaged. Hence, the radially inward projection length of the linear bodies 121 from the inner surface 111 is shortened or reduced in the vicinity of the proximal portion 104 or in the proximal portion 104. On the other hand, it is preferable that the sliding resistance is decreased or reduced to the largest extent in order to make it possible for the medical device to move more smoothly in the lumen 101 in the intermediate portion 105 of the catheter main body 100. Hence, the linear bodies 121 disposed in the intermediate portion 105 project from the inner surface 111 of the tubular body 110 toward the inner side in the radial direction such that it is possible to decrease the sliding resistance.

In the catheter main body 100, a melted portion 125 formed of the melted linear bodies 121 disposed in the proximal portion 104 is formed. The linear bodies 121 do not have their original shape in the melted portion 125. The melted portion 125 is fused with the tubular body 110. As described above, the linear bodies 121 disposed in the proximal portion 104 are melted to the extent that the linear bodies do not have the original shape, and thus, it is possible to suitably prevent a problem that the medical device, which is inserted from the proximal opening portion 104a, is caught from occurring. The projection length of the linear bodies 121 in the proximal portion 104 is not particularly limited as long as it is possible to inhibit or prevent the problem that the medical device is caught or the like from occurring.

Similar to the proximal portion 104, the projection length of the linear bodies 121 radially inward may be shorter in the distal portion 103 than in the intermediate portion 105 of the catheter main body 100. Even in a case of such a configuration, when the medical device is inserted into the lumen 101 via the distal opening portion 103a, it is possible to suitably prevent the medical device from being caught on the linear bodies 121. In addition, similar to the proximal portion 104, the melted portion 125, in which the linear bodies 121 are melted, may be formed in the distal portion 103. For example, in a case where the distal tip 150 is attached to the catheter main body 100 by fusion, it is possible to form the melted portion 125 when the distal tip 150 is attached.

As described above, the medical elongated body 10 according to the embodiment includes the elongated catheter main body 100. When the catheter main body 100 has the tubular body 110 made of the first resin and the reinforcing member 120 disposed on the inner surface 111 of the tubular body 110, which forms the lumen 101 of the catheter main body 100. The reinforcing member 120 is formed of the plurality of linear bodies 121 which are braided and has the gap portions 123 between the plurality of linear bodies 121 which are braided. The tubular body 110 has the convex portions 113 that penetrate the respective gap portions 123 on the inner surface 111 of the tubular body 110. In the linear body 121, at least an outer circumferential surface of the linear body 121 is formed of the second resin. The first resin is fused with the second resin in a state in which the convex portions 113 penetrate the respective gap portions 123. The melting point of the first resin is lower than the melting point of the second resin.

The kink resistance or tensile strength of the medical elongated body 10 configured as described above is improved by the reinforcing member 120 provided on the inner surface 111 of the tubular body 110. In addition, when the medical device is inserted into the lumen 101 of the catheter main body 100, the contact area between the inner surface 111 of the tubular body 110 and the medical device is decreased due to the reinforcing member (braided linear bodies 121) 120 disposed on the inner surface 111 of the tubular body 110. Therefore, the medical device that is inserted into the lumen 101 of the catheter main body 100 has a low sliding resistance against the inner surface 111 of the tubular body 110.

Since the tubular body 110 and the reinforcing member 120 both include the resin, the tubular body 110 and the reinforcing member 120 are rather easily fused together, compared to a case where the reinforcing member 120 is formed of metal. Further, since the convex portions 113 made of the first resin penetrate the respective gap portions 123 of the second resin of which the reinforcing member 120 is configured, and the convex portions are fused therein, a contact area between the first resin and the second resin increases, and thus it is possible to achieve relatively strong fusion between the tubular body 110 and the reinforcing member 120.

In addition, the melting point of the first resin of the tubular body 110 is lower than the melting point of the second resin included in the reinforcing member 120. Therefore, when the reinforcing member 120 is disposed in the tubular body 110, the reinforcing member 120 may not be melted due to the heat of fusion of the first resin and the second resin, but it is possible to maintain a shape of the reinforcing member 120. In this manner, it is possible to more suitably exhibit a function of reducing the sliding resistance of the medical device.

Since the reinforcing member 120 includes the second resin, the reinforcing member 120 and the tubular body 110 are well fused together. Therefore, when the end portion of the catheter main body 100 is cut and the distal tip 150 or the hub 160 is attached, there is no need to perform the end-portion treatment for preventing dispersion of the end portion of the reinforcing member 120, and thus it is easy to perform the manufacturing operation.

In addition, a length of the convex portion 113 of a site penetrating the gap portion 123 can be less than twice the thickness of the linear body 121 on the cross section perpendicular to the axial direction of the catheter main body 100. In this manner, it is possible to prevent the convex portions 113 from projecting radially inward more than the gap portions 123, and it is possible to suitably decrease the sliding resistance that acts between the inner surface 111 of the tubular body 110 and the medical device.

In addition, the linear body 121 is formed of a wire having a circular cross-sectional shape. In this manner, it is possible to decrease the contact area between the reinforcing member 120 and the medical device that is inserted through the lumen 101 of the catheter main body 100, and thus it is possible to more suitably decrease the sliding resistance.

In addition, the linear bodies 121 are formed of only the second resin. In this manner, it is possible to prevent the reinforcing member 120 and the guide wire from being scratched against each other when the metal medical device such as the guide wire is inserted through the lumen 101 of the catheter main body 100, and it is possible to suitably prevent the guide wire W from being damaged or broken. Further, regarding the catheter main body 100, since the tubular body 110 and the linear bodies 121 are formed of only the resin when a molding process is performed by using a mold or the like, it is possible to adjust the outer diameter, thickness, hardness, or the like by using fluidity of the resin. Therefore, the catheter main body 100 is also excellent in processability.

In addition, the outer layer 130 configured or made of a resin having a melting point higher than the first resin and is disposed on the outer surface of the tubular body 110. In this manner, when heat is applied from the side of the outer layer 130, it is possible to suitably prevent the reinforcing member 120 from receiving an influence of the heat. Further, since it is possible to melt the tubular body 110 that is disposed on the outer layer of the reinforcing member 120 such that the reinforcing member 120 and the outer layer 130 are fused together, it is possible to bond the reinforcing member 120 to the outer layer 130 while the shape of the reinforcing member 120 is suitably prevented from being damaged even in a case where the melting point of the outer layer 130 approximates the melting point of the reinforcing member 120.

In addition, the reinforcing member 120 includes at least one of the linear bodies which is recessed in a site where the plurality of linear bodies 121a and 121b intersect each other. In this manner, since the linear bodies 121a and 121b are strongly caught on each other, it is possible to still better maintain the tubular shape of the reinforcing member 120.

In addition, the catheter main body 100 has a hub 160 that holds the proximal end of the catheter main body 100, the distal portion 103 provided with the distal tip 150, the proximal portion 104 fixed to the hub 160, and the intermediate portion 105 extending between the distal portion 103 and the proximal portion 104. The linear bodies 121 project inward from the inner surface 111 of the tubular body 110 in the second region 105 and project less from the inner surface 111 of the tubular body 110 in the proximal portion 104 than in the intermediate portion 105. Therefore, it is possible for the medical device to rather smoothly move in the intermediate portion 105 of the catheter main body 100, and it is possible to suitably prevent the medical device from being caught on the linear bodies 121 in the vicinity of the proximal portion 104.

Modification Example 1

Next, a catheter main body 200 according to Modification Example 1 of the second embodiment will be described with reference to FIGS. 13(A) and 13(B). In the following description of the modification example, features that are similar to those described above are identified by a common reference numeral and a detailed description of such features is not repeated.

Figure 13A:
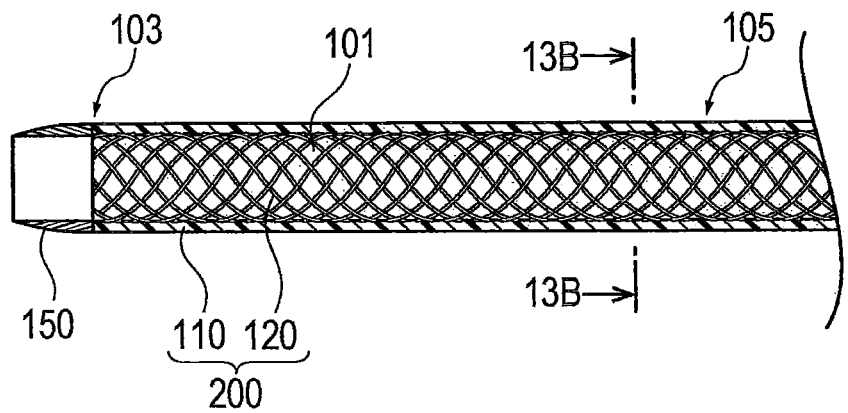
FIG. 13(A) is a view showing a longitudinal cross-section of a distal portion of a medical elongated body according to Modification Example 1 of the second embodiment.
Figure 13B:
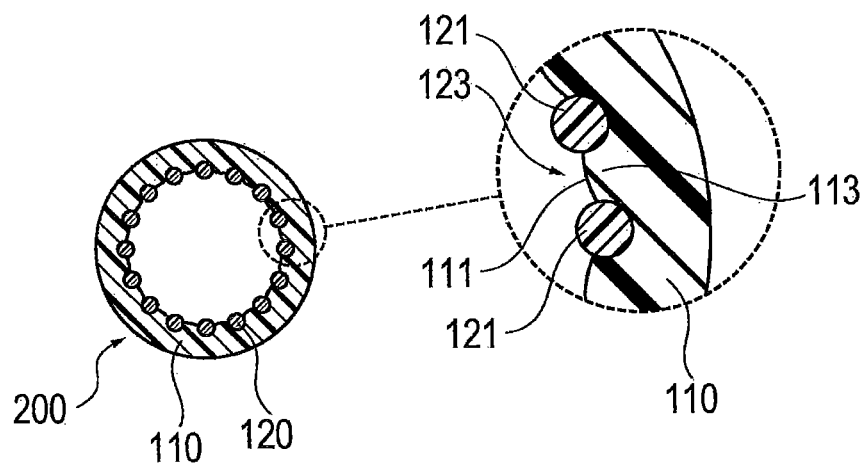
FIG. 13(B) is a view showing an axially orthogonal cross-section taken along the section line 13B-13B shown in FIG. 13(A).

As shown in FIGS. 13(A) and 13(B), the catheter main body 200 may not include the outer layer 130. In other words, the catheter main body 200 can be configured to include only the tubular body 110 made of the first resin and the reinforcing member 120. Even in a case of such a configuration, a part of the tubular body 110 is melted, and the tubular body 110 and the reinforcing member 120 are fused together. In this manner, it is possible to provide the medical elongated body 10 by which it is possible to decrease the sliding resistance that acts between the medical device and the tubular body. In addition, since it is possible to reduce the number of members to the extent that the outer layer 130 is not used, it is possible to achieve a decrease in manufacturing costs.

Modification Example 2

Next, the reinforcing member 320 according to Modification Example 2 of the second embodiment will be described with reference to FIG. 14. In the following description of the modification example 2, features that are similar to those described above are identified by a common reference numeral and a detailed description of such features is not repeated.

Figure 14:
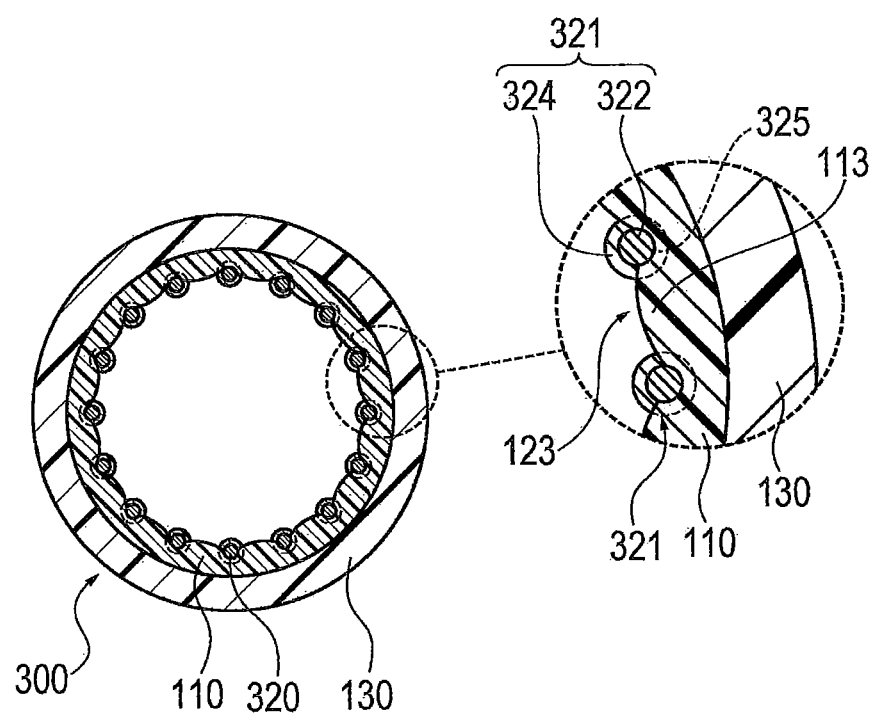
FIG. 14 is a view showing an axially orthogonal cross-section of a catheter main body according to Modification Example 2 of the second embodiment.

As shown in FIG. 14, the linear bodies 321 constituting the reinforcing member 320 can be configured to have a core material 322 made of metal and a second resin 324 that covers an outer circumferential surface of the core material 322, for example.

It is possible to use, as metal of the core material 322, various types of metal wires made of stainless steel, tungsten, copper, nickel, titanium, a piano wire, a cobalt-chromium based alloy, a nickel-tungsten based alloy (superelastic alloy), a copper-zinc based alloy, or an amorphous alloy.

It is possible to use, as an example of the second resin, a resin that is the same as the second resin that is used in the embodiment described above.

The use of the linear bodies 321 having the core material 322 made of metal enables a catheter main body 300 to have still more improved tensile strength. In addition, as shown in FIG. 14, a part of the second resin 324 is melted, and a site 325, in which the second resin and the inner surface 111 of the tubular body 110 are fused together, is formed. In this manner, the bonding strength between the linear bodies 321 and the tubular body 110 is increased. In this manner, since the core material 322 is strongly fixed to the tubular body 110, it is possible to suitably prevent a problem that the core material 322 is dispersed or the like from occurring.

The linear body 321 having a circular cross section is exemplified; however, similarly, a linear body that is formed to have a cross-section with an elliptical or rectangular shape other than the circular shape can also have the core material 322.

As described above, the inventive medical elongated body disclosed here is described in the embodiments and the plurality of modification examples; however, the present invention is not limited to only the configurations described in the embodiments and the modification examples, and it is possible to perform appropriate modifications within the scope of the claims.

For example, the medical elongated body may not be provided with the distal tip or the anti-kink protector. In addition, a special use of the medical elongated body is not particularly limited as long as the medical elongated body can be used for one purpose of guiding the medical device (the guide wire, various types of medical instruments for the medical treatment, or the like) into the living body.

In addition, the medical elongated body may have a configuration in which at least the melting point of the first resin is lower than the melting point of the second resin, and the first resin and the second resin are fused together in locations in which the convex portions of the tubular body penetrates the gap portions of the reinforcing member. It is possible to appropriately modify a configuration or the like other than the configurations described in the embodiments.

In addition, the catheter main body including the tubular body and the reinforcing member described in the second embodiment can be used as the inner tube (inner tube shaft) of the balloon catheter like that described in the first embodiment, for example.

The detailed description above describes embodiments of a balloon catheter and a medical elongated body representing examples of the inventive a balloon catheter and a medical elongated body disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A balloon catheter comprising:
an outer tube that includes a lumen;
an inner tube disposed in the lumen of the outer tube, the inner tube comprising a tubular body possessing an open proximal end and an open distal end, the tubular body including a guide wire lumen that communicates with both the open proximal end and the open distal end and through which a guide wire is insertable;
an outwardly expandable balloon fixed to a distal portion of the inner tube and a distal portion of the outer tube;
the tubular body being comprised of a first resin and a reinforcing member disposed on an inwardly facing surface of the tubular body that faces toward the guide wire lumen;
the reinforcing member including a linear body comprised of a second resin that is different from the first resin, the linear body projecting inwardly from the inwardly facing surface of the tubular body;
the inner tube including a first region at a distal portion of the inner tube, a part of the distal portion of the inner tube including the open distal end;
the inner tube also comprising a second region positioned proximal of the first region;

the reinforcing member being located in the first region of the inner tube and in the second region of the inner tube; and the linear body projecting inwardly from the inwardly facing surface of the tubular body less in the first region of the inner tube than in the second region.

2. The balloon catheter according to claim 1, wherein the inner tube includes a distal tip disposed in the first region of the inner tube.

3. The balloon catheter according to claim 1, wherein the inner tube includes a boundary region between the first region and the second region, the linear body projecting inwardly from the inwardly facing surface of the tubular body by a projection length, the projection length of the linear body in the boundary region being reduced from the second region toward the first region.

4. The balloon catheter according to claim 1, wherein the linear body projects inwardly from the inwardly facing surface of the tubular body by a projection length, the inner tube including a third region positioned proximal of the second region, and the projection length of the linear body being less in the third region than in the second region.

5. The balloon catheter according to claim 4, wherein the inner tube includes a boundary region between the third region and the second region, the linear body projecting inwardly from the inwardly facing surface of the tubular body by a projection length, the projection length of the linear body in the boundary region being reduced from the second region toward the third region.

6. The balloon catheter according to claim 1, wherein the reinforcing member is formed of a plurality of linear bodies which are braided.

7. The balloon catheter according to claim 6, wherein the linear body is configured of a circular or elliptical wire.

8. The balloon catheter according to claim 1, wherein the linear body is comprised of a core material made of metal and the second resin that covers an outer circumferential surface of the core material.

9. The balloon catheter according to claim 1, wherein the linear body is comprised of only the second resin.

10. The balloon catheter according to claim 1, further comprising: an outer layer comprised of a resin possessing a melting point higher than the melting point of the first resin, the outer layer being disposed on an outer surface of the tubular body.

11. A balloon catheter comprising:
an outer tube that includes a lumen;
an inner tube disposed in the lumen of the outer tube, the inner tube comprising a tubular body possessing an open proximal end and an open distal end, the tubular body including a guide wire lumen that communicates with both the open proximal end and the open distal end and through which a guide wire is insertable;
an outwardly expandable balloon fixed to a distal portion of the inner tube and a distal portion of the outer tube;
the tubular body being comprised of a first resin and a reinforcing member disposed on an inwardly facing surface of the tubular body that faces toward the guide wire lumen;
the reinforcing member including a linear body comprised of a second resin that is different from the first resin, the linear body projecting inwardly from the inwardly facing surface of the tubular body;
the inner tube including a first region at a distal portion of the inner tube, a part of the distal portion of the inner tube including the open distal end;

the inner tube also comprising a second region positioned proximal of the first region;

the reinforcing member being located in the first region of the inner tube and in the second region of the inner tube;

the first and second resins of the tubular body in the first region being melt-solidified, the first and second resins of the tubular body in the second region being melt-solidified; and the first and second resins of the tubular body in the first region being more melt-solidified than the first and second resins of the tubular body in the second region.

12. The balloon catheter according to claim 11, wherein the open proximal end of the tubular body is located at an intermediate portion of the outer tube located between proximal and distal ends of the outer tube.

13. A medical elongated body comprising:
an elongated catheter main body that includes a lumen,
the catheter main body comprising a tubular body made of a first resin and a reinforcing member disposed on an inwardly facing surface of the tubular body that faces toward the lumen of the catheter main body, the reinforcing member being made of a second resin different from the first resin; the reinforcing member being comprised of a plurality of linear bodies which are braided so that gaps exist between adjacent linear bodies which are braided, the linear bodies each possessing an outer circumferential surface;
the tubular body including convex portions that each project inwardly from the tubular body and penetrate a respective one of the gap portions;
at least an outer circumferential surface of the linear body being comprised of the second resin;
the first resin being fused with the second resin at locations in which the convex portions penetrate the gap portions; and
a melting point of the first resin is lower than a melting point of the second resin.

14. The medical elongated body according to claim 13, wherein a length of each of the convex portions penetrating the gap portions is shorter than twice a thickness of the linear body on a cross-section be perpendicular to an axial direction of the catheter main body.

15. The medical elongated body according to claim 13, wherein the linear body is a wire having a circular or elliptical cross-section.

16. The medical elongated body according to claim 13, wherein the linear body comprises a core material made of metal and the second resin that covers an outer circumferential surface of the core material.

17. The medical elongated body according to claim 13, wherein the linear body is made of only the second resin.

18. The medical elongated body according to claim 13, further comprising: an outer layer comprised of a resin having a melting point higher than the first resin and is disposed on an outer surface of the tubular body.

19. The medical elongated body according to claim 13, wherein the reinforcing member includes at least one of the linear bodies which is recessed in a site where the plurality of linear bodies cross each other.

20. The medical elongated body according to claim 13, further comprising:
a hub that holds a proximal end of the catheter main body;
the catheter main body possessing a distal portion provided with a distal tip, a proximal portion fixed to the hub, and an intermediate portion extending between the distal portion and the proximal portion; and the linear body projecting inwardly from an inwardly facing surface of the tubular body in the intermediate portion, and inwardly projects less in the proximal portion than in the intermediate portion.

* * * * *